United States Patent
Ausserlechner et al.

(10) Patent No.: US 8,442,787 B2
(45) Date of Patent: May 14, 2013

(54) APPARATUS, SENSOR CIRCUIT, AND METHOD FOR OPERATING AN APPARATUS OR A SENSOR CIRCUIT

(75) Inventors: Udo Ausserlechner, Villach (AT); Mario Motz, Wernberg (AT); Christian Kolle, Villach (AT)

(73) Assignee: Infineon Technologies AG, Neubiberg (DE)

( * ) Notice: Subject to any disclaimer, the term of this patent is extended or adjusted under 35 U.S.C. 154(b) by 369 days.

(21) Appl. No.: 12/771,310

(22) Filed: Apr. 30, 2010

(65) Prior Publication Data

US 2011/0270553 A1  Nov. 3, 2011

(51) Int. Cl.
*G01R 13/04* (2006.01)
*G01R 17/00* (2006.01)
*G01R 17/06* (2006.01)
*G01R 13/28* (2006.01)

(52) U.S. Cl.
USPC ............ 702/64; 702/57; 702/59; 702/65

(58) Field of Classification Search ............ 702/64, 702/99, 104, 141, 182, 183, 189; 324/249; 700/109; 714/26

See application file for complete search history.

(56) References Cited

U.S. PATENT DOCUMENTS

| | | | |
|---|---|---|---|
| 5,041,780 A | 8/1991 | Rippel | |
| 5,173,680 A | 12/1992 | Kumagai | |
| 5,795,997 A | 8/1998 | Gittins et al. | |
| 6,204,658 B1 | 3/2001 | Stanusch et al. | |
| 6,424,018 B1 | 7/2002 | Ohtsuka | |
| 6,566,872 B1 * | 5/2003 | Sugitani | 324/249 |
| 6,934,596 B2 * | 8/2005 | Yoshida et al. | 700/109 |
| 6,940,265 B2 | 9/2005 | Hauenstein et al. | |
| 7,184,930 B2 * | 2/2007 | Miyasaka et al. | 702/183 |
| 7,259,546 B1 | 8/2007 | Hastings et al. | |
| 7,302,357 B2 | 11/2007 | Ausserlechner et al. | |
| 7,437,260 B2 | 10/2008 | Ausserlechner et al. | |
| 7,882,394 B2 * | 2/2011 | Hosek et al. | 714/26 |
| 2005/0217126 A1 | 10/2005 | Inoue | |
| 2009/0108839 A1 | 4/2009 | Ausserlechner | |

FOREIGN PATENT DOCUMENTS

| | | |
|---|---|---|
| DE | 10233129 A1 | 2/2003 |
| EP | 1849683 A1 | 10/2007 |
| WO | 0123899 A1 | 4/2001 |
| WO | 2005033718 A1 | 4/2005 |

* cited by examiner

*Primary Examiner* — Michael Nghiem
*Assistant Examiner* — Felix Suarez
(74) *Attorney, Agent, or Firm* — Escheweiler & Associates, LLC

(57) ABSTRACT

An apparatus is described, including: a signal processing circuit adapted to process an input signal to obtain an output signal; a sensor element for sensing a predetermined physical quantity, wherein the sensor element is adapted to generate a sensor signal in response to the predetermined physical quantity; wherein the signal processing unit is adapted to process the input signal to obtain the output signal depending on the sensor signal; and wherein the apparatus further comprises an evaluation circuit adapted to evaluate the sensor signal and to generate an indication signal indicating an abnormal operating condition in case the sensor signal does not fulfill a predetermined normal operation criterion.

12 Claims, 8 Drawing Sheets

APPARATUS, SENSOR CIRCUIT, AND METHOD FOR OPERATING AN APPARATUS OR A SENSOR CIRCUIT

TECHNICAL FIELD OF THE INVENTION

Embodiments of the present invention relate to apparatus comprising a sensor element, sensor circuits and methods of operating the same.

BACKGROUND OF THE INVENTION

Often sensors are used in applications, where ultimate reliability and prevention of misuse or fraudulent manipulation is crucial: life sustaining applications in medical treatment, applications in transportation where lives may be endangered in case of malfunction, metering, billing and remote payment systems which need protection against forgery or fraudulent falsification.

Applications for magnetic sensors in general and for differential magnetic sensors in particular are, for example, systems counting the rotations of a mechanical member, for example for measuring the amount of water flowing through a pipe or measuring the number of turns of a wheel in a car, that must be protected against manipulation by electromagnetic stimuli. For example, one could try to apply a rotating magnetic field to such a sensor system to imitate the rotation of the mechanical member thereby manipulating the number of rotations detected. The rotating field could be generated by attaching a permanent magnet to a handheld drilling machine or by using two orthogonal coils supplied with two sinusoidal currents with 90° phase shift.

Another example refers to electricity meters, where one could try to attach a small permanent magnet nearby a sensor in an intend to defraud. If the current through a conductor is measured, for example using a magnetic sensor, one could try to bend the conductor so that the current flows in opposite direction and close to the original sensor thereby reducing the magnetic field on the sensor which would decrease the measured value of apparent current.

Besides intentional misuse as described above, it is beneficial if these sensor systems are also robust against unintended manipulation, or put more general, against abnormal operating conditions. For example, if a rotational position sensor is exposed to a large magnetic field this may impair its accuracy. In an automotive system this may lead to a wrong ignition timing with increased fuel consumption and increase air pollution. In medical instrumentation this may lead to inaccurate determination of a three dimensional location (3D-location) of a micro-surgery tool during a delicate heart- or brain-surgery.

Therefore, there is a need to make sensors or systems using such sensors robust against manipulation or against an abnormal operating condition and/or to detect, whether a manipulation or an abnormal operating condition occurs.

SUMMARY OF THE INVENTION

Embodiments of the invention provide an apparatus, comprising: a signal processing circuit adapted to process an input signal to obtain an output signal; a sensor element for sensing a predetermined physical quantity, wherein a sensor element is adapted to generate a sensor signal in response to the predetermined physical quantity; wherein the signal processing unit is adapted to process the input signal to obtain the output signal depending on the sensor signal; and wherein the apparatus further comprises an evaluation circuit adapted to evaluate the sensor signal and to generate a signal indicating an abnormal operating condition in case the sensor signal does not fulfill a predetermined normal operation criterion.

Embodiments of the evaluation circuit can be adapted to output the signal, also referred to as an evaluation signal, only in case abnormal operation conditions have been detected or can be adapted to output the signal in any case, wherein, e.g., a first value of the signal indicates a normal operating condition and a second value different from the first value indicates the abnormal operation condition. The signal generated by the evaluation circuit in case it detects an abnormal operation condition can also be referred to as an abnormal operation condition signal.

The signal or evaluation signal produced by the evaluation circuit is not to be confused with a sensor signal or measurement signal, e.g. a temperature value output by a temperature sensor which represents the temperature but does not comprise any evaluation or assessment of the temperature with regard to the operating conditions at which the temperature signal was measured. In other words, in contrast to sensor signals or measurement signals, the evaluation signal does not represent the physical quantity to be measured but comprises, e.g., information about an evaluation or assessment whether the operating conditions at which the sensor signals and measurements signals were obtained are to be considered normal or not. In case the evaluation indicates that the operating conditions are normal, the sensor signals and the measurement signals (or any other output signal produced by the signal processing unit) can be considered, e.g., "trustworthy" or "reliable", whereas in case the evaluation signal indicates that the operating conditions are not normal or abnormal, the sensor signals and measurement signals (or any other output signal produced by the signal processing unit) can be considered "not trustworthy" or "unreliable".

Embodiments of the invention provide a sensor circuit comprising: a first primary sensor element adapted to generate a first primary sensor signal in response to a first primary physical quantity comprising a first wanted part or a first unwanted ambient part; and a second primary sensor element adapted to generate a second primary sensor signal in response to a second primary physical quantity comprising a second wanted part or a second unwanted ambient part, wherein the second primary physical quantity is of a same type as the first physical quantity; a signal processing circuit adapted to process the first primary sensor signal and the second primary sensor signal according to a first algorithm to obtain a measurement signal; and an evaluation circuit adapted to evaluate the first primary sensor signal and the second primary sensor signal according to a second algorithm that is different than the first algorithm and to generate a signal indicating an abnormal operating condition in case the result of the second algorithm sensor signal does not fulfill a predetermined normal operation criterion.

Embodiments of the invention provide a sensor circuit comprising: a signal processing unit adapted to process at least one sensor signal of a plurality of sensor signals generated by at least one sensor element to obtain a measurement signal; and an evaluation circuit adapted to evaluate the at least one sensor signal of the plurality of sensor signals to derive a signal indicating an abnormal operating condition in case the at least one sensor signal does not fulfill a predetermined normal operation criterion, wherein the predetermined normal operation criterion defines a predetermined relation between a value of the at least one sensor signal and a value of at least one other sensor signal of the plurality of sensor signals during a normal operation, or a relation between the value of the at least one sensor signal and a value of a measurement signal during a normal operation.

In certain embodiments, the plurality of sensor signals can be produced by the same sensor element or other sensor elements of the same class of sensor elements over time to evaluate a temporal relation between the at least one sensor signal and the at least one other sensor signal or the measurement signal.

In further embodiments, the plurality of sensor signals can be produced by different sensor elements of the same class of sensor elements, i.e. by sensor elements adapted to measure the same type of physical quantity, to evaluate a spatial relation between the at least one sensor signal and the at least one other sensor signal or the measurement signal.

In even further embodiments, the plurality of sensor signals can be produced by different sensor elements of different classes of sensor elements, i.e. by sensor elements adapted to measure different types of physical quantities, and the evaluation circuit can be adapted to evaluate a temporal or spatial relation between the at least one sensor signal and the at least one other sensor signal or the measurement signal. For example, in case a high current flows through a magnetic current sensor, the temperature due to internal heat generation increases. This effect or other similar effects can be used to evaluate a primary sensor signal based on a secondary sensor signal.

Embodiments of the invention provide a method for operating an apparatus comprising a sensor element for sensing an predetermined physical quantity, the method comprising: sensing the predetermined physical quantity by the sensor element and generating a sensor signal in response to the predetermined physical quantity; processing an input signal to obtain an output signal depending on the sensor signal; and evaluating the sensor signal and generating a signal indicating an abnormal operating condition in case the sensor signal does not fulfill a predetermined normal operation criterion.

Embodiments of the invention provide a method for operating a sensor circuit comprising a first primary sensor element and a second primary sensor element, the method comprising: generating a first primary sensor signal by the first primary sensor element in response to a first primary physical quantity comprising a first wanted part or a first unwanted ambient part; and generating a second primary sensor signal by the second primary sensor element in response to a second primary physical quantity comprising a second wanted part or a second unwanted ambient part, wherein the second primary physical quantity is of a same type as the first physical quantity; processing the first primary sensor signal and the second primary sensor signal according to a first algorithm to obtain a measurement signal; and evaluating the first primary sensor signal and the second primary sensor signal according to a second algorithm that is different than the first algorithm and to generate a signal indicating an abnormal operating condition in case the result of the second algorithm sensor signal does not fulfill a predetermined normal operation criterion.

Embodiments of the invention provide, for example, an apparatus or a sensor system that is robust against external disturbances. In other words, embodiments of the invention relate to apparatus and/or sensor systems capable to detect abnormal operating conditions, wherein "abnormal operating conditions" are operating conditions which are significantly different from normal operating conditions.

Normal operating conditions are, for example given in a datasheet of the electronic system. The datasheet, for example lists the supply voltage, the ambient temperature, for sensor systems also a certain range of applied values for the physical quantities to be measured. It may also comprise environmental quantities like a maximum allowed radiation dose or ambient pressure or humidity or a range of allowed altitudes or a maximum acceleration or vibration. Those operating conditions can also be referred to as "explicitly given normal operating conditions".

Many operating conditions are not given explicitly, but rather implicitly, for example, if the datasheet explains a rule for soldering or mounting a device into a module or how to fix it to a heat slug or how to bend its leads. Any violation of this rule may lead to operating conditions which are far from normal, for example, lead to too high mechanical stress or temperature during assembly and potentially also during operation, which again might deteriorate the measurement quality.

The term "abnormal operating conditions" should not be confused with "defects" or "defective systems". For example, (i) a high density memory may detect that a certain address space of the memory is stuck at zero or one, or (ii) a telecommunication system may detect that errors have occurred during storage or transmission of data which is done by error coding techniques like the well known Reed-Solomon-Code for compact disks for audio recording, or (iii) a sensor system may detect that part of a large array of sensor elements may be defective because it renders signals which differ significantly from the rest of the sensor array although the entire array is exposed to the same pressure, temperature or magnetic field, or whatever physical quantity is measured by the sensor array. Neither such defects nor other internally generated defects, for example, production flaws, nor defects caused by some external origin like damage due to electrostatic discharge (ESD) or insufficient cooling or too high supply voltage or reverse polarity of voltage to certain input/output ports (I/O-ports) of the electronic system shall be confused with the "abnormal operating conditions" addressed by embodiments of the invention.

Abnormal operating conditions may also lead to a system error, but this is not necessarily the case. Abnormal operating conditions—in contrast to the defects detected in the system as explained above—often cause less obvious effects compared to these "defects", for example, reduced quality of the system which is not yet classified as "erroneous" or faulty, for example, enhanced noise, inaccurate processing of signals, inaccurate readings of sensor values, reduced lifetime (e.g. due to increased stress on the system), or reduced reliability (e.g. higher bit error rates, reduced speed for data transmission). Moreover, the presence of abnormal operating conditions may also be a sign that there is something wrong with the environment or ambient conditions in which the system is working. Finally, abnormal operating conditions may also be the result of intentional misuse of the system by a user or by sheer vandalism, for example in billing systems users may try to manipulate the system.

To distinguish the "abnormal operating conditions" discussed herein from the above "defects", the abnormal operating conditions can also be referred to as "abnormal ambient conditions" or "abnormal ambient operating conditions" as embodiments of the invention relate to the detection of abnormal ambient conditions. Such abnormal ambient conditions or environmental conditions have the effect, typically only temporarily, i.e. without causing lasting damage to the sensor or system, that the sensor or system does not behave or perform as expected, e.g. as expected under normal ambient conditions.

Therefore, there is also a need to detect, whether an abnormal ambient operating condition occurs, e.g. whether the abnormal ambient operating condition exceeds certain limits between which the sensor or the system performs acceptably, and to signal this exceeding of the certain limits, for example, to a controller. By detecting an abnormal ambient operating condition, sensors or systems using such sensors can be made more robust against manipulation (e.g. against a manipulation by applying an external physical quantity disturbing the normal operation of the apparatus or system forming an intended case of abnormal ambient operating conditions to achieve a specific effect at the sensor or system) or unintended worsening of the ambient operating conditions such that the ambient operating conditions become abnormal.

Sensors are used to transduce a physical quantity into a sensor signal, the sensor signal representing a property of the physical quantity. The physical quantity to be measured by the sensor element may also be referred to as a physical measurand and can be, for example a magnetic field, temperature, mechanical stress, etc. The sensor signal can be, for example, a voltage or a current which is primarily or essentially dependent on a physical, quantity to be measured. For example, in case of a Hall sensor for measuring a magnetic field, the polarity and voltage value or current value of the sensor signal output by the Hall sensor primarily depends on the polarity and strength of a magnetic field measured by the Hall sensor. In addition, the sensor signal typically also depends on other ambient physical quantities, for example a temperature or a mechanical stress applied to the Hall sensor. However, the influence of a temperature and mechanical stress is typically much smaller than the influence or dependence of the sensor signal from the primary physical quantity to be measured by the sensor element. Therefore, in case of a Hall sensor which is designed for measuring the physical quantity "magnetic field", the magnetic field may be referred to as the "primary physical quantity" (the physical quantity the sensor is designed to sense or measure) and these other physical quantities may also be referred to as the "secondary physical quantities" (the physical quantities the sensor is not designed to sense or measure but which influence the measurement of the primary physical quantity of the sensor, e.g. by causing a drift). The influence of these secondary physical quantities on the measurement of the primary physical quantity can be compensated, for example, by implementing secondary sensor elements adapted to transduce these secondary physical quantities into corresponding sensor signals and to adapt the operation or readout of the primary sensor element to achieve a measurement of the primary physical quantity that is essentially independent of one or several of such secondary physical quantities, e.g. by compensating the drift of a magnetic field measurement signal generated by a magnetic field sensor due to temperature or mechanical stress. In other words, the secondary physical quantity can be any physical quantity that is different from the primary physical quantity or belongs to a different type of physical quantity, wherein, for example, the magnetic field forms a first type of physical quantity, the temperature a second type of physical quantity and the mechanical stress a third type of physical quantity.

As the range of sensor signals and measurement values for normal operation conditions are known, they can be evaluated with regard to their expected characteristics or values (expected for normal operation conditions). Therefore embodiments of the evaluation circuit can be adapted to evaluate the sensor signal or sensor signals based on static or dynamic expected characteristics of the sensor signals and the measurement signals derived therefrom to detect abnormal operation conditions.

Further embodiments of the apparatus or sensor circuit use the fact that different sensor signals typically show a certain relation during normal operation conditions which can be used to detect whether an abnormal operation conditions is present. This relation may be temporal or spatial.

Ambient physical quantities like ambient temperature typically show a homogeneous spatial characteristic. This can be used by embodiments, which comprise e.g. several (at least two) temperature sensor elements as secondary sensor elements, to evaluate continuously, whether these temperature sensor elements really measure the same temperature. In case the difference between at least two temperature sensor elements becomes too large, an abnormal ambient condition can be signaled.

Magnetic fields of a current to be measured by a magnetic field current sensor typically show an inhomogeneous spatial characteristic. For example due to the radial characteristic of the magnetic field and/or due to the structure or geometry of the conductor, e.g. due to changing cross sections, notches within the current conductor and/or due to bending of the current conductor. In contrast thereto, the unwanted earth's magnetic field superposing the wanted magnetic field of the current to be measured is spatially (and temporally) homogeneous, at least with regard to the dimensions of sensor circuits. Furthermore, other current conductors near to the current sensor also produce an unwanted magnetic field, which superposes to the wanted magnetic field produced by the current to be measured. This unwanted magnetic field may show an inhomogeneous spatial characteristic (radial, etc), however, this inhomogeneous spatial characteristic is different from the spatial characteristic of the current to be measured. For example, in case of a magnetic current sensor with two magnetic field sensor elements arranged on opposite sides of the primary conductor of the magnetic current sensor and with the same distance to the primary conductor, the wanted magnetic field of the current to be measured has the same magnitude at both magnetic field sensor elements but with a different sign. A parallel other current conductor would also produce a radial magnetic field, however, this unwanted magnetic field would have different magnitudes at the locations of the two magnetic field sensor elements and would have the same sign. Thus, the wanted and unwanted magnetic field parts can be distinguished by their different spatial characteristics.

Therefore, embodiments of the apparatus or sensor circuits can use the knowledge of the specific spatial (or temporal) characteristic of the wanted physical quantities and evaluate, whether the sensed or measured physical quantity at least essentially shows the expected characteristic, and signal an abnormal operation condition in case the deviation of the sensed or measured characteristic of the physical quantity differs too much from the expected one. In other words, embodiments can verify, whether the sensor signals and the measurement signal are consistent, i.e. reflect the expected spatial or temporal dependencies, and produce the abnormal operation condition signal in case the signals or measurement signal are not consistent or at least not sufficiently consistent.

Thus, further embodiments comprise a current sensor circuit comprising: a signal processing unit adapted to process at least one sensor signal of a plurality of sensor signals generated by at least one magnetic field sensor element to obtain a measurement signal; and an evaluation circuit adapted to evaluate the at least one sensor signal of the plurality of sensor signals using the at least one other sensor signal or the measurement signal to derive a signal indicating an abnormal operation condition in case the at least one sensor signal does not fulfill a predetermined normal operation criterion, wherein the predetermined normal operation criterion is derived from a predetermined temporal or spatial relation between a value of the at least one sensor signal and a value of at least one other sensor signal of the plurality of sensor signals during a normal operation condition.

The larger the degree of the spatial or temporal inhomogeneity of the wanted physical quantity, the more difficult it becomes for a person trying to manipulate the apparatus or sensor circuit to imitate this characteristic and the better becomes the protection of the apparatus or sensor circuit against intended manipulation but also against any unintended disturbing physical quantity.

Particular embodiments of the invention relate to a class of systems which is particularly prone to operating conditions because the systems measure environmental or ambient physical quantities: sensor systems.

Typical electronic sensor systems are adapted to measure at least one physical quantity and output the result of this measurement by at least one signal. To this end sensors have to interact more immediately with their environment than other electronic systems. Therefore, sensor systems or sensors in general are more susceptible to general environmental influences or ambient conditions. In fact, typically, sensors are adapted to measure at least one primary physical quantity, yet the measurement of this at least one primary physical quantity is typically influenced by at least one secondary physical quantity. For example, a Hall sensor is adapted to measure a component of a magnetic field (i.e. a magnetic field component which may comprise wanted and unwanted parts) applied to it, yet it is also sensitive to temperature changes or mechanical stress applied to it. A further example is a magneto-resistive sensor that is adapted to measure one component (i.e. a magnetic field component with a first three-dimensional orientation) of the magnetic field, yet the magneto-resistive sensor is also sensitive to a second perpendicular component of the magnetic field (i.e. a second magnetic field component with a second three-dimensional orientation orthogonal to the first orientation).

According to a further aspect of the invention, embodiments of the sensor circuit comprise more than one sensor element adapted to measure the same physical quantity or the same type of physical quantity. A particular class of such sensor systems comprising two or more sensor elements of the same type or class are called "gradiometers". Gradiometers detect a spatial variation of a primary physical quantity. A simple example is a differential Hall sensor which measures a difference in a magnetic field on two spots or locations on the semiconductor substrate. The two spots are, for example 2.5 mm spaced apart from each other. The advantage of gradiometers is that they allow to separate disturbances or unwanted parts or portions of the primary physical quantity from the wanted part or portion of the physical quantity. An example is a magnetic current sensor, which has two Hall plates and a wire in between both of them. The current through the wire generates circular magnetic field lines so that both Hall plates, which are located symmetrical to the wire, for example, on opposite sides of the wire with regard to the current flow through the wire, detect the same magnitude of the field, yet with a different sign. The signal processing circuit according to this differential sensor principle subtracts the signals of both Hall plates, each of the signals including, for example a wanted part (the magnetic field produced by the current flowing through the wire) and an unwanted part (the earth's magnetic field or any other background magnetic field), which effectively doubles the contributions of the circular field lines (the wanted parts), yet the earth's magnetic field (the unwanted part) is identical on both Hall plates (identical with regard to the sign and orientation of the magnetic field) and, therefore, is cancelled after the subtraction of the two total measured primary physical quantities. Therefore, the differential sensor principle allows to separate the unwanted magnetic field part from the earth from the wanted field part of the current flowing through the wire.

This example, also shows a second property of gradiometers: redundancy. The described system has two Hall plates to measure only one current. The signal of the second Hall plate is redundant in the absence of any background fields because it is the signal of the first Hall plate multiplied by "−1". So the second Hall plate renders no additional information on the current to be measured. Yet, it renders information, if there is a background field present because then it is different from the field on the first Hall plate multiplied by "−1" and the difference is twice the background field. In other words, adding the sensor signal of the first Hall plate and the sensor signal of the second Hall plate cancels the wanted signal part (because they are essentially equal in magnitude, however not in sign) and results in providing a value representing the strength and orientation of the earth magnetic field or any other homogeneous magnetic field multiplied by 2. An evaluation circuit (EC) may compare the value of this homogeneous magnetic field with a predetermined value like e.g. 20 mT and it outputs "abnormal operating condition" if the homogeneous magnetic field exceeds this value. Then the system works perfectly (i.e. with negligible error) at normal operating condition and it signals "abnormal operating condition" when the homogeneous field is so large that it endangers proper operation of the system.

In general terms, an n-th order gradiometer consists of n+1 sensor elements of the same type or same class. It can be used to derive a primary physical quantity and to detect n spatial derivatives of the primary physical quantity, namely the $0^{th}$ order spatial derivative (which corresponds to the homogeneous portion of the primary physical quantity which does not depend on the location), the first order spatial derivative (which corresponds to the slope), the second order spatial derivative (which corresponds to the curvature), etc. and finally the $(n-1)^{th}$ order spatial derivative. One out of all these spatial derivatives can be used for the determination of the measurand and all other spatial derivatives can be used to check for violation of normal operating conditions. The n-th spatial derivate scales with the n-th power of the size of the system, which for integrated sensor systems is on the order of several millimeters or less.

Embodiments of the invention can be adapted to detect manipulation or abnormal ambient conditions on an integrated circuit through on-board sensors (like for magnetic field, temperature or mechanical stress) by processing their readouts through algorithms and comparing the results with predetermined fixed or dynamic limits over a specific time and signal this via output ports to an external controller.

In many cases it is good practice to use a differential field measurement: to this end the system samples, for example, a magnetic field component at two locations and subtracts both of them. One important advantage of this measurement system is that it cancels homogeneous background fields (like e.g. Earth's field or the stray field of motors and other electromagnetic actuators).

Specific embodiments of the invention can be adapted to detect manipulation on differential magnetic field sensors by using the redundant information supplied by the multitude of sensor elements on the die by processing their readouts through algorithms and comparing the results with predetermined fixed or dynamic limits over a specific time and signal this via output ports to a controller.

BRIEF DESCRIPTION OF THE DRAWINGS

Embodiments are described herein after, and make reference to the appended drawings.

Figure 1A:
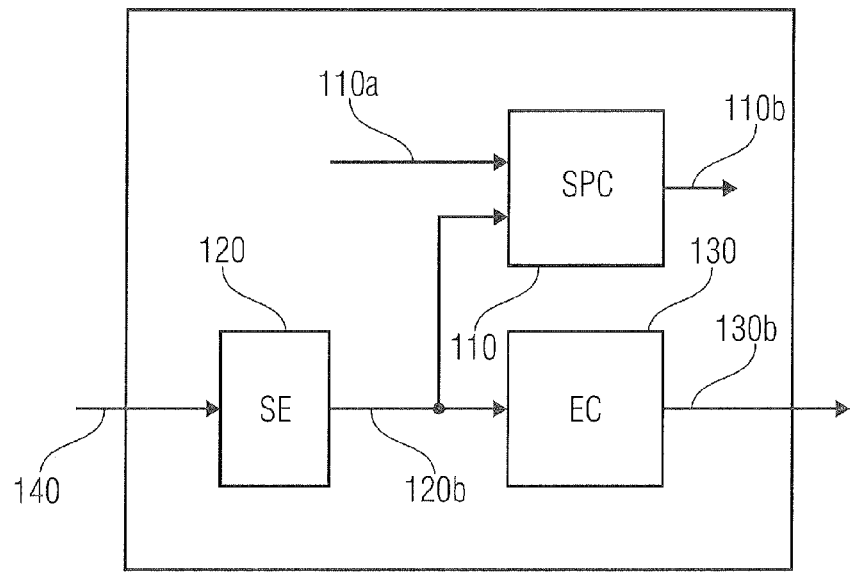
FIG. 1A shows a schematic embodiment of an apparatus comprising a sensor element and an evaluation circuit.

Equal or equivalent elements or elements with equal or equivalent functionalities are denoted in the following description of the Figures by equal or equivalent reference numerals.

DETAILED DESCRIPTION OF THE INVENTION

FIG. 1A shows a block-diagram of an embodiment of an apparatus comprising a signal processing circuit (SPC) 110, a sensor element (SE) 120 and an evaluation circuit (EC) 130. The signal processing circuit 110 is adapted to process an input signal 110a to obtain an output signal 110b. The sensor element 120 is adapted to sense a predetermined physical quantity 140, for example an ambient physical quantity 140, which may have an influence or impact on the signal processing circuit 110, wherein the sensor element 120 is adapted to generate a sensor signal 120b depending on or in response to the predetermined physical quantity 140.

The predetermined physical quantity, e.g. temperature or mechanical stress, can have, for example, an unwanted influence on the input signal 110a itself or on the processing of the input signal by the signal processing circuit 110, e.g. may cause a deviation of the input signal, e.g. a drift due to a variation of the temperature. Therefore, the signal processing circuit 110 is adapted to process the input signal 110a, to obtain the output signal 110b depending on the sensor signal 120b (see arrow), for example to compensate for the drift caused by the temperature variation.

In a specific embodiment, as described later based on FIG. 2, the input signal 110a can be a signal generated by a primary sensor, wherein the sensor signal 120b is used to compensate the drift of the signal 110a to facilitate a measurement less prone or essentially independent of temperature variations.

The evaluation circuit 130 is adapted to evaluate the sensor signal 120b and to generate a signal 130b indicating an abnormal operating condition in case the sensor signal 120b does not fulfill a predetermined normal operation criterion or normal operation condition, or defined in a positive way, in case the sensor signal 120b does fulfill a predetermined abnormal operation criterion or abnormal operation condition.

In the following embodiments, the invention will be primarily described based on a negative definition of the criterion, i.e. the abnormal operation condition is obtained in case a sensor signal does not fulfill a predetermined normal operation criterion. However, it should be born in mind that both, positive or negative definitions can be equally applied to achieve the same result. Therefore, explanations given with regard to the negative definition of the criterion apply in a corresponding manner to the positive definition of the decision criterion.

In other words, the evaluation circuit 130 is adapted to obtain a characteristic of the sensor signal and to generate the signal 130b in case the characteristic of the sensor signal 120b does not coincide with an expected characteristic of the sensor signal that is indicative of a normal operation.

The sensor element 120 can be adapted to transduce a secondary ambient physical quantity or a primary physical quantity, for example, an unwanted primary ambient physical quantity, which may be, e.g. an unwanted ambient part of a primary physical quantity.

The sensor elements described herein can be adapted to produce a sensor signal in response to a physical quantity the respective sensor element is adapted to sense or measure, wherein the sensor signal output by the sensor element can be a continuous analogue signal representing the respective physical quantity comprised of time continuous analogue values. In alternative embodiments, the sensor elements can be adapted to comprise analogue-to-digital-converters (ADC) and to convert the analogue and continuous signal output, for example, by a Hall plate or magnetic field measurement or a voltage produced by a negative temperature coefficient resistor (NTC) or positive temperature coefficient resistor (PTC) into a series of digital sensor signals or sensor signal values, i.e. a sequence of discrete sensor signals or sensor signal values over time, and to output these digital values as sensor signal 110a or 120b.

The abnormal operation criterion may define or may be derived from, e.g. a threshold the sensor signal shall not exceed during normal operation (because the drift of the input signal cannot be compensated sufficiently any more, or because the measurement deviation or processing deviation of the input becomes too large). The abnormal operation criterion may define or may be derived from a maximum value and a minimum value, the sensor signal shall not exceed (the normal operation range being defined as the range between the minimum and the maximum value), or may define or may be derived from a maximum temporal deviation magnitude the sensor signal shall not exceed (the normal operation range being defined by deviations of the sensor signal over time below the maximum temporal deviation magnitude). Further, the abnormal operation criterion may be derived from a sign or polarity the signal should not have, an average value (e.g. in case wanted ambient physical quantities have a known frequency f or period T and unwanted or abnormal ambient physical quantities have a different frequency or period), or frequency contributions the sensor signal should not have (e.g. in case wanted ambient physical quantities have a known frequency limited spectrum).

The abnormal operation criterion can further comprise or define tolerances for the above or other criteria to consider noise or other influences onto the sensor signal and the evaluation of the sensor signal to avoid, e.g. false detections of abnormal operation conditions due to the above influences, and to, thus, achieve a more reliable detection of truly abnormal ambient or operation conditions.

According to one embodiment, the predetermined normal operation criterion defines a maximum value of the sensor signal 120b, and the evaluation circuit is adapted to compare a value of the sensor signal with the maximum value and to generate the signal 130b indicating an abnormal operating or ambient condition in case the value of the sensor signal is higher than the maximum value. In addition or instead of the aforementioned maximum value, the predetermined normal operation criterion may also define a minimum value of the sensor signal 120b, and the evaluation circuit may be adapted to compare the value of the sensor signal with the minimum value and to generate the signal 130b in case the value of the sensor signal 120b is smaller than the minimum value.

According to a further embodiment, the maximum value or the minimum value is a zero value. Thus ambient physical quantities that have a sign, polarity or orientation different from an expected or acceptable sign, polarity or orientation of the ambient physical quantity can be detected and the signal 130b to indicate an abnormal ambient condition is generated and, e.g., output by the apparatus 100. The expected or acceptable sign, polarity or orientation of the ambient physical quantity defines, e.g., the normal ambient or operation condition of the physical quantity.

In other embodiments, the sensor element is adapted to generate a plurality of sensor signals 120b over time, for example a temporal sequence of sensor signals, in response to the ambient physical quantity, wherein the temporal sequence of sensor signals represents the physical quantity over time, including any variations of the physical quantity over time. To obtain the temporal sequence of sensor signals the apparatus comprises, e.g., a time basis, either for each circuit element individually or centrally for some or all circuit elements. The time base can, e.g., be a oscillator or a simple RC low-pass filter, which separates fast variations from slow variations.

In further developments of such other embodiments, the predetermined normal operation criterion can define a maximum magnitude for a change of the sensor signal over time, and the evaluation circuit can be adapted to compare a magnitude of a change of the sensor signal over time with the maximum magnitude for a change of the sensor signal and to generate the signal 130b in case the magnitude of the change of the sensor signal over time is higher than the maximum magnitude for a change of the sensor signal. The predetermined abnormal operation criterion can define, for example, the maximum magnitude for a change of the sensor signal between two consecutive sensor signals or between two sensor signals with a predetermined time difference. This method can also be referred to as a temporal gradient detection method.

In further developments of such other embodiments using a plurality of sensor signals obtained at different time instants by the sensor element, the predetermined normal operation criterion can define an maximum average value of the sensor signal for a predetermined duration, and the evaluation circuit can be adapted to determine an average value of the sensor signal for the predetermined duration and to generate the signal in case the average value of the sensor signal is higher than the maximum average value of the sensor signal. For such further developments the predetermined normal operation criterion may define—additionally or alternatively to the maximum average value—a minimum average value of the sensor signal for a predetermined duration (the same duration as for the maximum average value or a different duration), and the evaluation circuit may be adapted to determine an average value of the sensor signal for the predetermined duration and to generate the signal in case the average value of the sensor signal is lower or smaller than the minimum average value of the sensor signal.

The predetermined duration may correspond to a period of the predetermined or ambient physical quantity at normal operation conditions, e.g. in case no unwanted part of the predetermined or ambient physical quantity is present, or to an expected or wanted physical quantity of the type of physical quantity to be measured by the sensor element 120, whereas an abnormal or unwanted physical quantity or part of the type of physical quantity to be measured is not periodic at all or has a different period T and, thus, can be detected because the average value obtained by the evaluation circuit 130 is smaller than the minimum average value or higher than the maximum average value.

In further developments of such other embodiments using a plurality of sensor signals obtained at different time instants by the sensor element, the predetermined normal operation criterion can define a maximum frequency of the sensor signal, wherein the evaluation circuit is adapted to process the plurality of sensor signals to obtain a spectral representation of the plurality of sensor signals and to generate the signal in case the spectral representation has a significant contribution at least one frequency that is higher than the maximum frequency. In further embodiments the predetermined normal operation criterion may additionally or alternatively define a minimum frequency of the sensor signal, wherein the evaluation circuit is adapted to process the plurality of sensor signals to obtain a spectral representation of the plurality of sensor signals and to generate the signal in case the spectral representation has a significant contribution at least one frequency that is smaller than the minimum frequency. A significant contribution can be, for example, any magnitude that is higher than a 10% or 20% of a maximum magnitude of the spectral representation.

In even further embodiments of the apparatus 100, the sensor element 120 is located at a first position of the apparatus, and the apparatus comprises a further sensor element (not shown in FIG. 1A or 1B) located at a second position of the apparatus for sensing the ambient physical quantity at the second position. In this case, the sensor element 120 is adapted to generate the sensor signal 120b depending on the ambient physical quantity 140 at the first position, and the further sensor element is adapted to generate a further sensor signal depending on the ambient physical quantity at the second position. In addition the predetermined normal operation criterion defines a maximum magnitude of a difference between the sensor signal 120b and the further sensor signal, and the evaluation circuit is adapted to evaluate a difference between the sensor signal and the further sensor signal and to generate the signal in case a magnitude of the difference is higher than a maximum magnitude of the difference between the sensor signal and the further sensor signal. This method can also be referred to as a spatial gradient detection method. The sensor signal and the further signal to be compared for the spatial gradient detection are, for example, generated at the same time, i.e. synchronously, or essentially the same time, i.e. without significant delay, wherein without significant delay means that the time difference between the measurement or sensing of the two signals is much smaller than the time scale of the disturbances that shall be detected. The latter can also be referred to as real-time measurement.

Figure 1B:
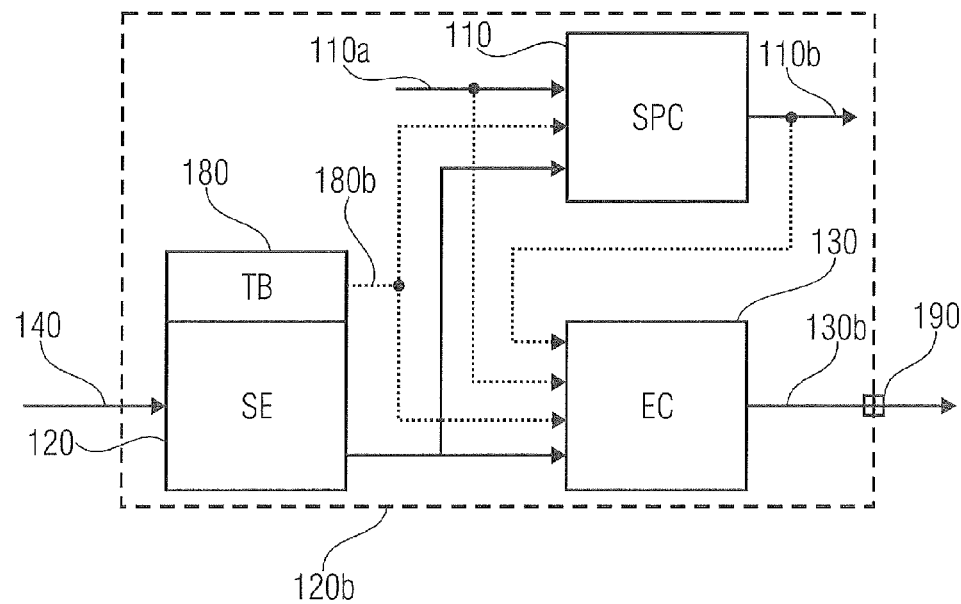
FIG. 1B shows a block diagram of an embodiment of an apparatus according to FIG. 1A comprising additionally a time base and a feedback of the output signal to the evaluation circuit.

FIG. 1B shows a block-diagram of an embodiment of an apparatus according to FIG. 1A, wherein the embodiment 100' of the apparatus comprises additionally a time-base (TB)

180 and an output port 190 for outputting the abnormal operation condition signal 130b. The dotted lines in FIG. 1B indicate optional features.

The output port can be any interface, for example, an electrical contact-based interface, e.g. an external contact or pad for electrically connecting the apparatus or sensor circuit to an external device via connecting wires or bond connections, or contact-less interface, e.g. an antenna or any other radio frequency interface, or an optical interface. The apparatus or sensor circuit is adapted to communicate the signal 130b via said output port, either instantaneously or delayed after meanwhile storage. Further embodiments of the apparatus or sensor circuit may comprise separate output ports for the signal 130b and the output signal or measurement signal 110b, or may use one common output port to output both, the signal 130b and the output or measurement signal 110b.

The time-base can be a filter element integrated into a sensor element 120. In an alternative embodiment, the time base 180 can be a separate oscillator unit, which is adapted to provide the sensor element 120 with a clock signal, for example, for analogue-to-digital-conversion or any other processing performed by the sensor element. In further embodiments, the time base 180 provides the clock signal 180b not only to the sensor element 120 but to other circuit elements of the apparatus, for example, to the signal processing circuit 110, the evaluation circuit 130 or to other sensor elements. In even further embodiments, each of the elements has its own time base or shares a time base with other elements of the apparatus.

In contrast to the apparatus according to FIG. 1A, the apparatus 100' comprises an evaluation circuit 130 that is adapted to receive the output signal 110b or measurement signal 110b and to perform the evaluation of the sensor signal 120b, i.e. the evaluation whether an abnormal operation condition exists, based on the measurement signal or output signal 110b.

Embodiments of the apparatus or the sensor circuits described herein can be adapted to evaluate the sensor signal using static criteria or thresholds, e.g. static minimum or maximum values or the sign of the sensor signal (i.e. criteria not depending on other sensor signals or the measurement signal), or using dynamic criteria or thresholds, e.g. criteria depending on other sensor signals or the measurement signal, and/or can be adapted to evaluate the sensor signal using only one or several other sensor signals, using only the output or measurement signal 110b, or using one or several other sensor signals and the output or measurement signal 110b for the evaluation.

Other embodiments of the apparatus and/or of the sensor circuit, as for example described in the following based on FIGS. 2 to 6, can also comprise an evaluation circuit 130 that is adapted to receive the measurement signal 110b for evaluating the sensor signal 120b. These other embodiments may also comprise the output port 190 to output the abnormal operation condition signal 130b, and/or may comprise one or more time base units 180 for providing clock signals 180b to the different elements of the sensor circuits.

Even further embodiments comprise an evaluation circuit 130 that is adapted to not only use the input or a sensor signal 120b for the manipulation evaluation but also the input signal 110a or a further sensor signal 110a and/or the output signal 110b or measurement signal 110b. The evaluation circuit can be further adapted to evaluate the sensor signal 120b of the sensor element 120 only in case the input signal 110a or the output signal 110b are small. For example, in case the apparatus 100 or 110' is a current measuring unit or current meter and the signal processing circuit 110 indicates a large current (i.e. a large signal or signal value 110b), the current meter 100, 100' can be adapted to not evaluate a sensor signal 120b to detect a manipulation. However, in case a measured current indicated by the measurement signal 110b is small (i.e. a measurement value 110b has a low value), it might be more important to exclude a manipulation and to perform an evaluation of the sensor signal 120b.

It should be noted that, in particular for apparatus with integrated sensor circuits, it is easy to determine the spatial distribution of a physical quantity over the chip surface because (i) the position or location of the different sensor elements can be controlled on a micrometer-level due to high-precision production techniques, (ii) production variations of the sensor elements can be kept small because the spacing of the elements integrated on a single chip or a single semiconductor die is very small, for example, only some few millimeters (in contrast to lot-to-lot or wafer-to-wafer or chip-to-chip variations in case different sensor elements are integrated into different chips or semiconductor dies), and (iii) the remaining variation, for example, of the sensor signal values due to the variation of the position or due to other production variations of the sensor elements themselves, can be equilibrated in an end-of-line test because the individual sensor elements remain on the same chip and are, thus, not mixed with sensor elements of other chips, which would be the case for discrete sensor elements, wherein "discrete" means that a single sensor element is implemented per chip.

It is further emphasized that in case a system, for example, an apparatus or a sensor circuit as described herein, is disturbed (intentionally or unintentionally) from external, the unwanted external physical quantity or external disturbing physical quantity has a spatial dependency that is smaller, the larger the distance between the source of the disturbance and the sensor elements is. One advantage of the integrated semiconductor technology now is the aspect of the miniaturization. Therefore, it is possible to design a current sensor such that the wanted primary physical quantity (the magnetic field of the current to be measured and flowing through a primary current conductor integrated into the package or even into the semiconductor substrate) causes a relatively strong spatial dependency on the sensor elements. For embodiments of housed apparatus, housed sensors, housed sensor circuits or housed sensor packages, the design of the housing or packaging is such that external disturbers have a certain minimum distance to the individual sensor elements so that the disturbing or unwanted physical quantities applied from external to the sensor elements only have a smaller spatial dependency. This can be easily achieved, for example by a plastic encasing or plastic encapsulation with sufficient dimensions, as will be described in more detail later with reference to FIG. 5B.

Figure 2:
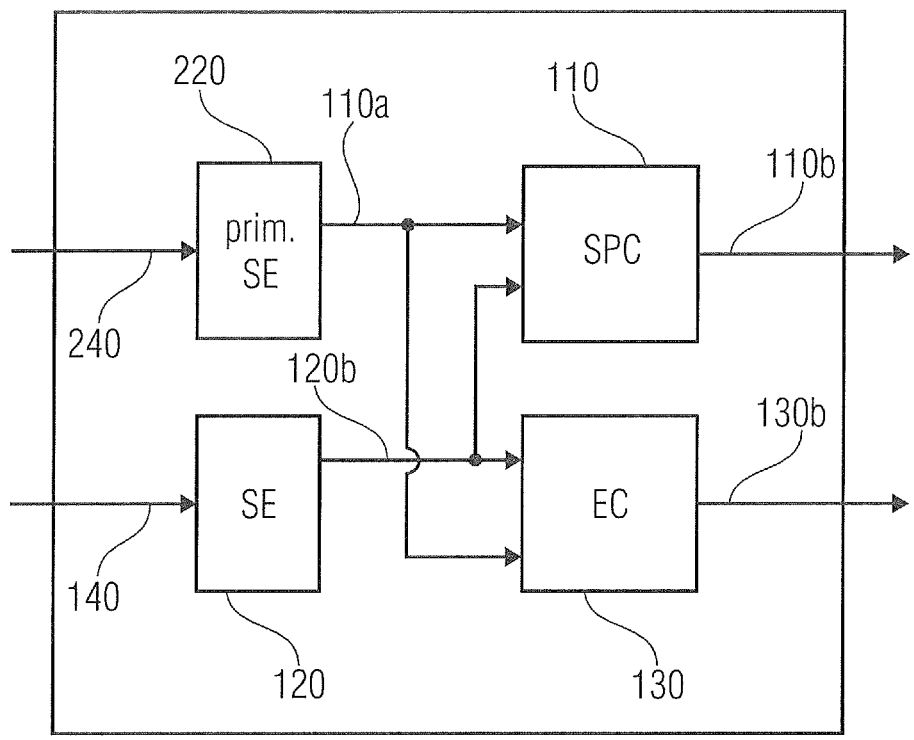
FIG. 2 shows a block diagram of an embodiment of a sensor circuit comprising a primary sensor element and an additional (primary or secondary) sensor element and an evaluation circuit.

FIG. 2 shows a block-diagram of a specific embodiment of the apparatus 100, wherein the apparatus 100 is a sensor circuit 200. The sensor circuit 200 comprises the signal processing circuit 110, the sensor element 120, the evaluation circuit 130 and additionally (compared to FIG. 1A) a primary sensor element 220. The primary sensor element 220 is adapted to transduce a primary physical quantity, or in other words, to generate a primary sensor signal 110a as input signal 110a in response to the primary physical quantity 240. The signal processing circuit 110 is adapted to process the primary sensor signal 110a depending on the sensor signal 120b to obtain a primary measurement signal as output signal 110b, wherein the primary measurement signal 110b represents a property of the primary physical quantity 240.

The sensor element 120 can be a secondary sensor element for measuring a predetermined secondary physical quantity or ambient secondary physical quantity, or can be a primary sensor element for measuring a predetermined primary physical quantity or ambient primary physical quantity or ambient part of a physical quantity of the same type of physical quantity as the primary physical quantity measured by the primary sensor element 220.

In case of a Hall sensor, the magnetic field to be measured forms the primary physical quantity, the temperature or mechanical stress form the secondary ambient physical quantity 140. The voltage output by the Hall sensor 220 (e.g. a Hall plate) depends on the field strength and polarity of the magnetic field measured by the sensor element and on the variation over time of the magnetic field 240 and, thus, comprises information about at least one property or several properties, for example field strength, polarity and variation over time, of the primary physical quantity. The sensor element 120 can, for example, also be adapted to provide a voltage signal as sensor signal 120b, wherein the voltage signal 120b represents at least one property of the secondary ambient physical quantity, for example a temperature value or mechanical stress value.

As explained previously, the signal processing circuit can be adapted to compensate drifts of the primary sensor signal caused by variations in temperature or mechanical stress with regard to the measurement signal 110b to reduce the unwanted effect of a secondary ambient physical quantities.

As for the apparatus 100, the sensor element 120 can be a secondary sensor element adapted to transduce a secondary ambient physical quantity (e.g. to compensate a drift of the primary sensor signal 110a), or a primary sensor element adapted to transduce an unwanted ambient part of a primary physical quantity, wherein the sensor signal 120b is used, for example, to reduce the effect of background magnetic field parts through differential measurement principles.

Embodiments of the sensor circuit 200 comprise an output port, e.g. an external contact or pad or a wireless interface, to output the primary measurement signal 110b.

Embodiments of the sensor circuit 200 may form a sensor package, wherein the primary sensor element 220, the sensor element 120, the signal processing unit 110 and the evaluation circuit 130 are fully or at least partially encapsulated by an encapsulating material, wherein the sensor circuit comprises an external contact to output the primary measurement signal 110b and optionally another external contact to output the abnormal operation condition signal 120b, and wherein the two external contacts are not covered or only partly covered by the encapsulation material. In further embodiments the sensor circuit is adapted to output the abnormal operation condition signal 120b via the same external contact or interface as the primary measurement signal 110b.

The primary sensor element 220, the sensor element 120, the signal processing unit 110 and the evaluation circuit 130 can be arranged on different semiconductor dies or chips (multi-chip package) or integrated on the same semiconductor die or chip (single chip package or single die package). In further embodiments all components of the sensor circuit, including further components not shown in FIG. 2, except for the external contacts are encapsulated or are hermetically sealed from the environment by the encapsulation material.

Integrating the primary sensor element 220, the sensor element 120, the signal processing unit 110 and the evaluation circuit 130 on one semiconductor die makes it more difficult to manipulate the sensor signals 110a and 120b from external (due to the integration and small dimensions of the connecting lines between the sensor elements and the signal processing circuit and in particular the evaluation circuit).

Furthermore, providing an ambient operational condition monitoring as provided by embodiments of such an integrated sensor circuit provides highly reliable miniature sensors. Design engineers using such integrated sensor circuit only need to read or monitor the abnormal ambient condition signal to verify the correct functioning of the sensor and may employ automatic or manual countermeasures in case an abnormal operating condition is signaled by the sensor.

The above explanations with regard to the packaging, the external contacts or interfaces and the integration on different or the same semiconductor dies applies in a corresponding manner to the apparatus 100 and other embodiments of sensor circuits described herein.

Figure 3:
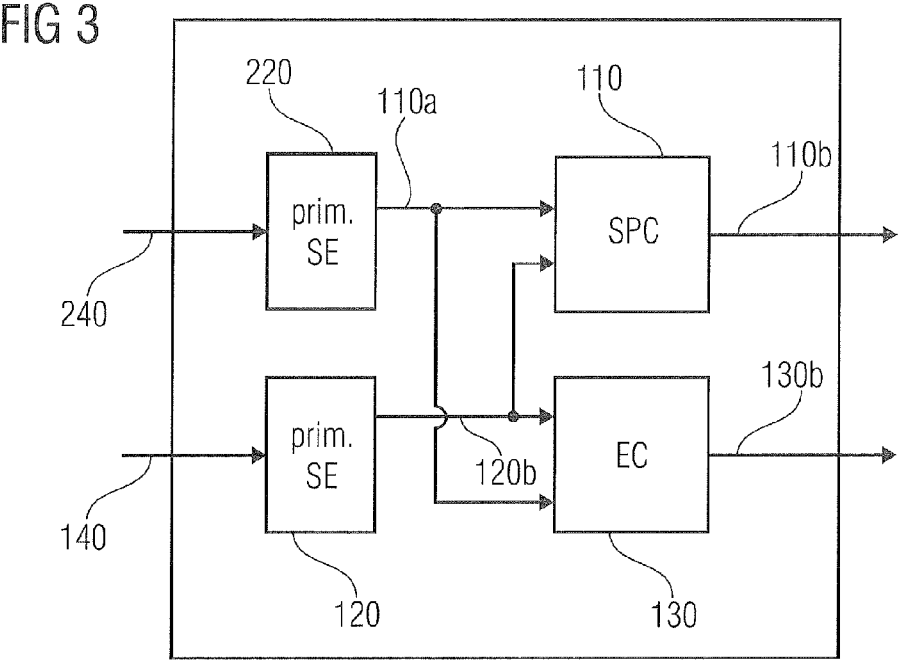
FIG. 3 shows a block diagram of an embodiment of a sensor circuit with two primary sensor elements arranged at two different locations of the sensor circuit and an evaluation circuit.

FIG. 3 shows a block-diagram of a specific embodiment of the sensor circuit according to FIG. 2, wherein the sensor element 120 is a further primary sensor element 120. Thus, the sensor circuit 300 comprises a first primary sensor element 220 and a second primary sensor element 120. First and second primary sensor elements are arranged at distinct locations, the first primary sensor element at a first location and the second primary sensor element 120 at a second location. The first primary sensor element 220 is adapted to measure the primary physical quantity at the first location or position, whereas the second primary sensor element 120 measures the primary physical quantity at the second location or position. The primary physical quantity measured or sensed by the first primary sensor element may comprise a first wanted part, e.g. a first wanted primary physical quantity part, and a first unwanted part, e.g. a first unwanted primary physical quantity part. The wanted and unwanted part may—depending on the context—also be distinguished by referring to the wanted part as "first primary physical quantity" or "first wanted primary physical quantity" and to the unwanted part as "first ambient primary physical quantity" or "first unwanted ambient primary physical quantity". This nomenclature correspondingly applies to the second physical quantity and the potentially comprised wanted and unwanted parts or portions thereof.

Further embodiments may comprise further (third, fourth, etc) primary sensor elements arranged at further (third, fourth, etc) locations of the sensor circuit to measure the primary physical quantity at the further locations and to produce in response to the primary physical quantity further (third, fourth, etc.) primary sensor signals being indicative of the primary physical quantity at the further locations or being indicative of at least one property of the primary physical quantity at the further locations. Any further location (third, fourth, etc.) is different to the first, second or other locations of other primary sensor elements. As for the first and second primary physical quantity, also the further primary physical quantities and the related further primary sensor signals may comprise wanted and unwanted parts, wherein with regard to the terms used to describe and/or distinguish both parts the same applies as explained for the first and second primary sensor signals in the preceding paragraph.

The sensor circuit 300 is, for example, a sensor circuit adapted to perform on one hand a differential measurement principle by subtracting the second primary sensor signal 120b from the first primary sensor signal 120a to obtain the measurement signal 110b. The sensor circuit is further adapted to evaluate on the other hand, whether the operating conditions are to be considered normal or abnormal, e.g. by adding the first primary sensor signal 110a and a second primary sensor signal 120b and comparing the sum of both with a threshold or maximum value, and to produce the abnormal operation condition signal in case the sum is higher than a certain threshold value.

In further embodiments, the signal processing circuit 110 is adapted to process the first 110a and second 120b primary sensor signals according to a first algorithm or function to obtain the primary measurement signal 110b, and the evaluation circuit 130 is adapted to process the first 110a and the second 120b primary sensor signals according to a second algorithm, which is different from the first algorithm, and to generate the abnormal operation condition signal 130b in case the result of the second algorithm does not fulfill a predetermined normal operation criterion.

The first algorithm may comprise subtracting the first primary sensor signal 110a or a multiple thereof from the second primary sensor signal 120b or a multiple thereof, or vice versa, and outputting the difference or a signal derived therefrom, e.g. a drift compensated version thereof, as measurement signal 110b.

The second algorithm may comprise adding the first primary sensor signal 110a or a multiple thereof and the second primary sensor signal 120b or a multiple thereof, and producing and outputting the abnormal operation condition signal 130b in case the sum is higher than a threshold value. In further embodiments, the second algorithm does not comprise subtracting the first primary sensor signal 110a or a multiple thereof from the second primary sensor signal 120b or a multiple thereof, or vice versa.

Further embodiments of the apparatus form an electronic sensor system which comprises at least two sensor elements 120, 220 which transduce the same physical quantity at two spots or locations into a first sensor signal 110a with a first sensor signal value and a second sensor signal 120b with a second sensor signal value, which further comprises a signal processing unit 110 adapted to output the output signal 110b or measurement signal 110b, which is a function of a difference of the value of the first sensor signal 110a and the value of the second sensor signal 120b, and which further comprises the evaluation circuit 130 that is adapted to supply a second signal 130b or abnormal operating condition signal 130b, which depends also on the value of the first sensor signal 110a and the value of the second sensor signal 120b, yet not on the difference of the value of the first sensor signal 110a and the value of the second sensor signal 120b.

Within the above context the term "function" refers to any function or algorithm, where for each input value x of the function f(x) the system or circuit gets an output value f(x). In a strict mathematical sense this should be unique, yet in the real sensor system this is only approximately unique, because it may be overlaid by random noise. However, in real sensor systems the function may be quantized so that the output value f(x) remains constant when x subtends within a sufficiently small range of a use, e.g. x1<x<x2 i.e., in case the input value x remains within a sufficient range of input values. Yet the function has no different values f(x) for the same value x.

Further embodiments comprise an electronic sensor system or sensor circuit which comprises at least three sensor elements which transduce the same physical quantity at three different spots or locations into a first sensor signal, a second sensor signal and a third sensor signal and output a first signal or measurement signal which is a function of the difference of the values of the first and the second sensor signal, and of the difference of the values of the second and third sensor signal, wherein the evaluation circuit generates or derives the signal 130b such that it is not obtainable by a sole sequence of mathematical operations performed on the output signal or measurement signal 110b. In other words, the function or algorithm used by the evaluation circuit processes the values of the sensor signals such that the result of the function has additional information on the physical quantity compared to the measurement signal 110b.

In even further embodiments, the electronic sensor system or sensor circuit comprises at least four sensor elements which transduce the same physical quantity at four different spots or locations into a first, a second, a third and a fourth sensor signal, wherein the signal processing circuit is adapted to output a measurement signal or output signal as a function of the difference of a value of the first sensor signal and a value of the fourth sensor signal, and as a difference of a value of the second sensor signal and a value of the third sensor signal, and wherein the evaluation circuit is adapted to supply the signal 130b depending on at least two values of the first, second, third or fourth sensor signal, and wherein the evaluation circuit is further adapted to process these at least two values of the sensor signal such that the result of the function or the signal 130b is not obtainable by a sole sequence of mathematical operations performed on the output or measurement signal 110b.

These and other embodiments for processing the first primary sensor signal 110a, the second primary sensor signal 120b and optionally further (third, fourth, etc.) primary sensor signals for obtaining the measurement signal 110b and/or for evaluating whether an abnormal ambient operation condition exists, will be explained in the following in conjunction with specific embodiments of the apparatus 100 and the sensor circuits 200, 300.

The two or more sensor elements adapted to measure the same type of physical quantity do not need to be of the same type of sensors. For measuring the temperature, embodiments can use, for example, a resistor or a diode, and, for example, in case the temperature is measured at two spots of the circuit or die, the temperature can be measured with a resistor on a first spot or location and with a diode as a second sensor element at the second spot or location. Hereafter, such different types of sensor elements for measuring the same physical quantity will be referred to as belonging to the same class of sensors or sensor elements, whereas different resistors for measuring a temperature are referred to belong to the same type (i.e. resistor type) of sensors or sensor elements.

Figure 4:
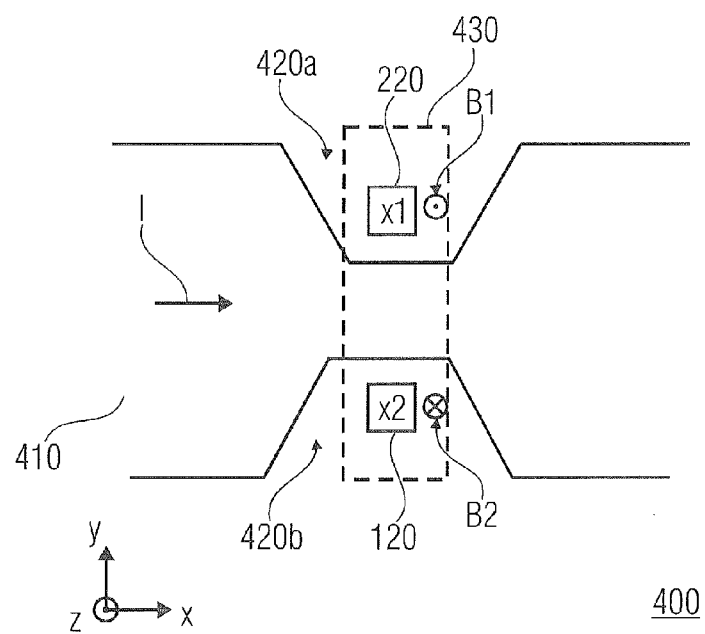
FIG. 4 shows a top-view of a magnetic field current sensor with two Hall sensor elements.

FIG. 4 shows a top view of an embodiment of a differential magnetic field sensor or differential magnetic field sensor circuit 300 implemented as, e.g. coreless, current sensor 400. The sensor circuit 400 comprises a first Hall sensor element or first Hall plate 220, a second Hall sensor element or Hall plate 120, which are arranged in a semiconductor die 430 on opposite sides of a current conductor 410 of the current sensor. The current I to be measured flows through the current conductor 410 and generates a radial magnetic field B that depends on the current density and the flow direction (see arrow) of the current to be measured. In case the current flows from left to right (with regard to the orientation of FIG. 4) the current produces a radial magnetic field B that has a positive z-orientation (with regard to the coordinate system as shown in FIG. 4, see $B_1$ being directed out of the picture) at a first location $x_1$, where the first primary sensor element 320 is located, and a negative z-orientation (with regard to the coordinate system as shown in FIG. 4, see $B_2$ being directed into the picture) at a second location $x_2$, where the second primary sensor element 120 is located. The signal processing circuit 110 and the evaluation circuit 130 are not shown in FIG. 4.

The current conductor 410 comprises notches 420a and 420b at opposed sides of the current conductor with regard to the flow direction of the current in order to increase the current density and, thus, the measurement sensitivity.

The first and the second sensor element 120, 220 are arranged with regard to their lateral position (x,y-plane, see coordinate system of FIG. 4) above or at least partially above the notches 420a, 420b, as close as possible to the conductor 410 and on opposite sides of the conductor with regard to the flow direction of the current. In case the notches 420a and 420b are symmetric and the first and second sensor element 220, 120 are arranged also symmetrically with regard to a central axis in the current flow direction of the current conductor, the first magnetic field measured by the first primary sensor element has the same magnitude as the magnetic field measured at the second primary sensor element 110 and the two only differ with regard to the sign or orientation of the measured magnetic field.

Further embodiments of the current sensor circuit 300 may comprise notches 420a, 420b with other geometries, only one notch or no notches at all. Other embodiments of the current sensor may comprise a wire as conductor, wherein the wire may be arranged in a straight manner or in a bent manner, e.g. in a meander like manner, and the primary sensor elements may be arranged on opposite sides of the wire.

Embodiments of the magnetic field current sensor 400 may also comprise the current conductor 410 as integral component or element of a current sensor package 400 to facilitate a fixed and accurate relative positioning of the hall sensors 220 and 120 with regard to the current conductor. In case a current needs to be measured, the whole package 400 can be connected to an external (with regard to the package itself) conductor for which the current shall be measured. Referring back to FIG. 4, the differential magnetic field sensor 400 measures the magnetic field B or a single component of the magnetic field at two locations $x_1$, $x_2$ to obtain a first primary sensor signal 110a representing the magnetic field or B-field $B_1$ at position $x_1$ and a second primary sensor signal 120b representing the magnetic field or B-field $B_2$ at position $x_2$. The signal processing circuit 110 computes the difference of the two sensor signals or sensor signal values representing the difference between the magnetic field at the two positions, i.e. the signal processing unit 110 computes the difference $B_1 - B_2$. The quantity to be measured or output as output or measurement signal 110b is a function of this difference: $Q = f(B_1 - B_2)$, wherein $B_1$ and $B_2$ may comprise wanted and unwanted magnetic field parts. This quantity or measured quantity may be the strength, sign, phase, frequency, ripple or duty-cycle of the current flowing through the current conductor, or an angular position or angular speed or angular acceleration of a target wheel in case of a magnetic rotation sensor as will be explained later based on FIG. 6.

Higher order differential systems have n magnetic sensor elements measuring the same component of the magnetic field on n different locations with n>2. They compute the quantity Q, for example, as a function of many differences according to:

$$Q = f(B_1 - B_2, B_2 - B_3, \ldots, B_{n-1} - B_n).$$

In other words, such measurement systems comprise 3 or more magnetic field sensors H1, H2, H3, etc. where the signals of two sensors elements are subtracted and the resulting terms are added up as a linear combination with fixed coefficients.

Figure 5A:
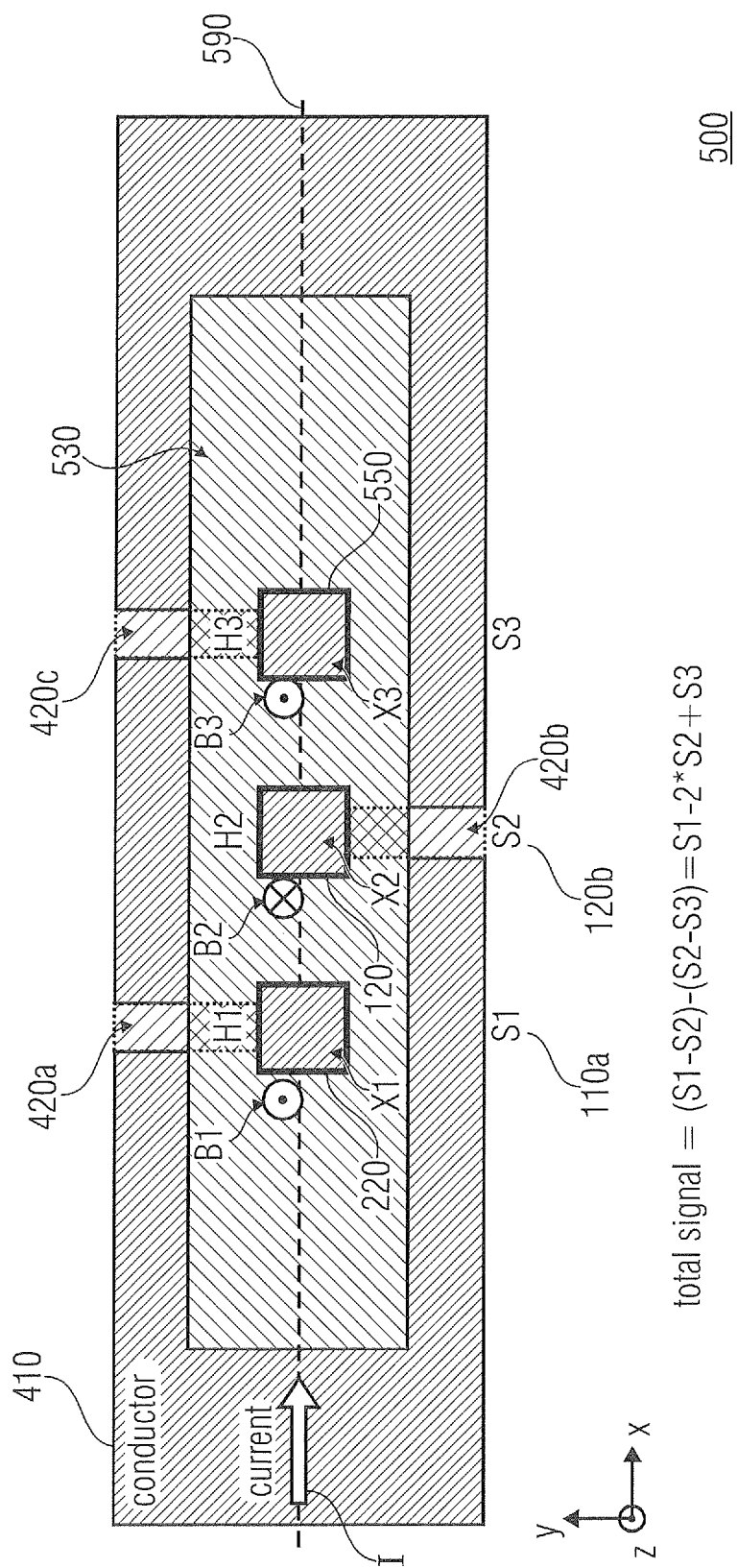
FIG. 5A shows a top-view of an embodiment of a magnetic field current sensor circuit with three Hall sensor elements.

FIG. 5A shows a schematic top-view of a magnetic current sensor or current sensor circuit 500 with three (n=3) Hall sensors 220, 120, and 520, respectively H1, H2 and H3 (the signal processing circuit and the evaluation circuit are not shown). Each of the Hall sensors H1, H2 and H3 is located at a different location $x_1$, $x_2$ and $x_3$ and measures the magnetic field $B_1$, $B_2$ and $B_3$ at the respective location of the Hall sensors. The current conductor comprises three slots, wherein each of the Hall sensors or Hall plates is arranged at least partially above one of the slots 420a, 420b and 420c and near to the current conductor 410. The first sensor element H1 produces the first sensor signal S1 (corresponds to 110a) in response to the magnetic field B1, the second sensor element H2 produces the first sensor signal S2 (corresponds to 120b) in response to the magnetic field B2, and the third sensor element H3 produces the first sensor signal S3 in response to the magnetic field B3. For embodiments with a conductor structure as shown in FIG. 5A (three slots 420a to 420c extending to the middle axis of the conductor and arranged in an alternating order on opposite sides of the current conductor with regard to the middle axis in current flow direction) and an arrangement of the Hall plates as shown in FIG. 5A (each of the Hall plates arranged above one of the slots and in a straight line above the mid axis or center axis 590 of the current conductor), the sign and magnitude of the sensor signals S1 and S3 are approximately the same, the magnitude of the sensor signal S2 is approximately a factor 2 higher than the magnitude of the sensor signals S1 or S3, and the sign of the second sensor signal is inverse or opposite to the signs of the first and third sensor signal S1 and S3. In case the current flows from left to right (according to the orientation of FIG. 5A) the sensor signals S1 and S3 have, for example, a positive sign and sensor signal S2 a negative sign. In case the current flows from right to left (according to the orientation of FIG. 5A) the opposite is true, the sensor signals S1 and S3 have, a negative sign and sensor signal S2 a positive sign. These relations between the magnitudes and the signs of the three sensor signals refer to the measurement of the magnetic field of the current I flowing through the current conductor 410 and do not consider any magnetic background fields, e.g. the earth's magnetic field. The earth's magnetic field, in contrast to the magnetic field of the current to be measured is homogeneous over the area of the current sensor 500, i.e. the earth's magnetic field superposes an additional ambient magnetic field or ambient magnetic field part, which is the same (due to its homogeneity) with regard to the sign and the magnitude for all three sensors H1 to H3.

The signal processing unit 130 is, for example, adapted to compute the current I flowing through the conducting strip 410 with the three slots according to $$I = (S1 - S2) - (S2 - S3) = S1 + S3 - 2 \cdot S2,$$

where S1, S2, S3 are the aforementioned signals of the planar Hall plates H1, H2, H3. Thus, as explained, the earth's magnetic field components are cancelled out, whereas the current is calculated as $I = 6 \cdot S$, in case $S1 = S3 = S$ and $S2 = -2 \cdot S$. Similarly any other homogeneous magnetic field, e.g. caused by a neighboring conductor or applied to manipulate the magnetic field current sensor, are cancelled out. In other words, the differential magnetic field current sensor is robust against such homogenous ambient magnetic fields. Since the sensor consists of 3 Hall elements at three locations it is a 2nd order gradiometer. Therefore it can cancel not only $0^{th}$ order spatial derivatives (=homogeneous background field) but also $1^{st}$ order spatial derivatives (=linear gradients of background field). However, magnetic fields with spatial derivatives of second or higher order might not be cancelled out and they may cause unacceptable measurement conditions, i.e. abnormal ambient operating conditions which cannot be detected by embodiments of the present invention. Therefore, the higher the grade of the gradiometer the better the detection of abnormal ambient conditions, e.g. applied to the sensor to manipulate the same.

The magnetic field parts produced by the current I to be measured form the first, second and third primary physical quantities or first, second and third wanted primary physical quantity parts, whereas the magnetic field parts produced by the earth magnetic field or any other ambient magnetic field source form the first, second and third ambient primary physical quantities or first, second and third unwanted primary physical quantity parts.

In the following further embodiments for detecting abnormal ambient conditions are described for magnetic field current sensors and, in particular for a differential current sensor as described based on FIG. 5A. If an intentional or unintentional manipulation of a sensor system is done with an externally applied magnetic field it can be distinguished from the wanted physical quantity Q by various means. In the following, with regard to a magnetic field current sensor circuit as described, for example, based on FIGS. 5A and 5B (but also based on FIG. 4), the magnetic field produced by the current flowing through the current conductor of the current sensor circuit is regarded as "internal magnetic field", whereas any magnetic field caused by any other source than the current flowing through the current conductor is regarded as disturbing magnetic field or external magnetic field (external with regard to the current sensor circuit and in particular with regard to the current sensor package), e.g. the earth's magnetic field or permanent magnets arranged next to the current sensor or magnetic fields generated by currents flowing through nearby conductors, etc, is regarded as "external magnetic field". Within this context one could interpret "external" also as "ambient", "unwanted" or "disturbing" and "internal" as "wanted". The externally applied magnetic field or ambient magnetic field may have, for example, a field strength exceeding a limit. In a current sensor with a full scale range of 100 A the magnetic field on the center Hall probe H2 is, e.g. 25 mT. So if 35 mT are detected by the Hall probe H2 or the evaluation circuit 130 this may be either due to an overcurrent event or to a manipulation with a permanent magnet brought in close proximity to the sensor.

Externally applied magnetic fields are likely to have a field pattern whose spatial dependence is markedly different from the field pattern generated by the wanted physical quantity Q. For example, in the current sensor of FIG. 5A with 3 slots in a strip of conductor, the field B generated by the current is highly inhomogeneous: it is positive on H1 and H3 and negative on H2. It is very difficult to externally apply a magnetic field via a permanent magnet which shows the same spatial dependence: not only must it have different signs on the 3 sensor elements, it must also have equal magnitudes on H1 and H3 and the magnitude on H2 must be equal to the sum of magnitudes on H1 and H3. Therefore several indicators can be used for detecting a manipulation or, in general, abnormal ambient conditions, as will be explained in the following.

As first indicator or criterion, the sum of the sensor signals or sensor signal values S1+S2+S3 must not exceed a certain threshold. Ideally the sum should be zero, in practice it should be, e.g., in a range within −10 mT (min. value for normal operation) and +10 mT (max. value for normal operation). In case the sum value S1−FS2+S3 exceeds these thresholds, the evaluation circuit is adapted to detect an abnormal ambient condition and to produce the signal 130b.

Other embodiments may also use a dynamic threshold like S1+S3−2*S2, which is directly related to the measurand Q, and may detect a manipulation or abnormal ambient condition if the following inequality is true:

$$abs(S1+S2+S3) > X*abs(S1+S3-2*S2),$$

where X is a weight factor and may have a value like 0.1, for example. The value of X adjusts the likelihood of manipulation or abnormal operation conditions.

In practice the accuracy of the sensor signals becomes poor for small signals so that a more robust algorithm for detecting abnormal ambient conditions can read as follows:

$$abs(S1+S2+S3) > \max(X*abs(S1+S3-2*S2); Y),$$

where max(a,b) is the larger value of a or b and Y is the above mentioned absolute limit like 10 mT.

A second criterion for detecting an abnormal ambient or operation condition is that S1 and S3 must not deviate too much from each other: ideally they should be equal, if no external field is applied. Manipulation or strong external fields are detected, if $$abs(S1/S2-1) > EPS,$$

EPS may be 0.1, for example. If EPS is small the detectability of manipulation is increased. EPS should be chosen such that the condition turns TRUE only if magnetic background fields exceed a level which notably deteriorates the measurement of Q. In practice one should blank out this condition, if S2 is close to zero by using the following condition:

$$abs((abs(S1)+X)/(abs(S2)+Y)-1) > EPS,$$

where X may be equal to Y. Generally X and Y should be chosen two to ten times larger than the zero-crossing error of the sensors. As zero-crossing error of a magnetic sensor, one denotes its output at zero field (e.g. offset of Hall sensors or coercivity of sensors involving soft magnetic parts). E.g. the residual offset of a spinning current integrated Hall sensor is about 50 µT and therefore X should be 50 to 500 µT, for example. In the above equations one may replace abs(x) with x^(2*n) with n=positive even integer number.

A third criterion for detecting an abnormal ambient or operation condition is that S1+S3 must not deviate too much from (−1)*S2: this is identical to the first criterion.

A fourth criterion for detecting an abnormal ambient or operation condition is that (−2)*S1 and S2 must not deviate too much from each other: this is identical to the first criterion combined with the second criterion.

A fifth criterion for detecting an abnormal ambient or operation condition is that (−2)*S3 and S2 must not deviate too much from each other: this is identical to the first criterion combined with the second criterion.

Summarizing the aforementioned: with 3 sensor elements S1, S2, S3 one may combine them in various linear combinations, yet only 3 of these combinations are essentially different—all others may be derived from superpositions of these three ones. One of these combinations can be used to find the measurand Q, or in other words can be used by the signal processing unit 110 to determine the measurement signal 110b. The other 2 linear combinations should be equal to zero in the case of vanishing magnetic disturbances or ambient magnetic fields. These 2 combinations can be used to estimate the background magnetic field and therefore they can be used by the evaluation circuit 130 to estimate if someone wants to manipulate the sensor or an abnormal ambient or operation condition exists.

A sixth criterion for detecting an abnormal ambient or operation condition is to evaluate the sign of the sensor signal S1, S2 or S3. The externally applied magnetic field may have, e.g., a sign that is opposite to the field from the wanted physical quantity or measurand Q. Referring again to the magnetic field current sensor 500 of FIG. 5A, if the polarity of the current is known then the polarity of the magnetic field on the 3 Hall plates is known. If the current flows in the direction shown in the figure then the out-of-plane component of the magnetic field on sensors H1 and H3 points out of the drawing plane while it points into the plane on sensor H2. If an external field is applied, it may have a wrong direction and this can be used to detect manipulation.

A seventh criterion for detecting an abnormal ambient or operation condition is to evaluate the average of one or several sensor signals. The externally applied magnetic field may have a temporal average that is opposite to the field from the wanted measurand Q or that is different from the average of the wanted measurand Q. If one considers a rotating code wheel with equal north and south poles along its perimeter the time average of the magnetic field on each sensor is zero (unless the observation period is shorter than the time during which one north- and south-pole pass in front of the sensor).

Figure 6:
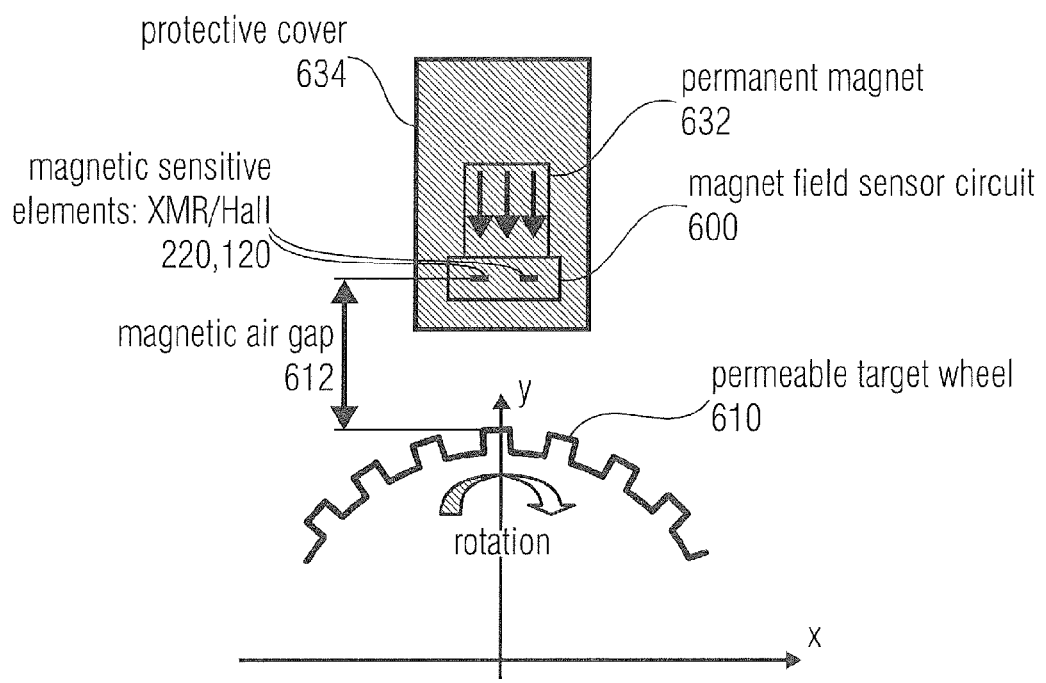
FIG. 6 shows a schematic view of a magnetic rotation sensor circuit with 2 magnetic field sensor elements at 2 locations.

FIG. 6 shows a schematic view of a magnetic rotation sensor circuit 600 comprising a first and a second primary magnetic field sensor 220 and 120, e.g. a Hall sensor or a magneto resistive sensor like an XMR sensor (the signal processing circuit and the evaluation circuit are not shown). The system shown in FIG. 6 further comprises a permanent magnet for biasing the magnetic field sensor circuit 600 and a protective cover 634 surrounding the permanent magnet and the sensor circuit. The target wheel 610 of which the rotation shall be measured by the magnetic rotation sensor 600 is, e.g. a toothed wheel made of iron with teeth at its periphery, and the two magnetic sensor elements are arranged at a distance 612, also referred to as magnetic air gap, from these teeth and continuously measure the magnetic field caused by the teeth and the gaps in between.

Similarly, the average of a purely sinusoidal current through a mains supply is zero, for integration times for example larger than 1/50 or 1/60 seconds. So the sensor system of a current meter, for example a current meter measuring the used current of a household, may simply integrate the output signal over a reasonably long time. If the result is larger than a predefined value the background field is too high.

Of course it is also possible to integrate the signal of each individual sensor in a differential sensor system—in fact this works also for an absolute sensor having only a single sensor element.

An eighth criterion for detecting an abnormal ambient or operation condition is to evaluate the spectrum of the measured magnetic field or physical quantity. The externally applied magnetic field may have significant spectral contributions outside the signal bandwidth of the wanted measurand Q. If one considers an energy meter for the mains supply it is clear that the dominant spectrum is close to the mains frequency 50 Hz or 60 Hz. If a manipulation with a significantly different frequency, e.g. below 40 Hz or above 70 Hz (or below 30 Hz or above 80 Hz), is undertaken this may be detected in the total signal or in the individual sensor signals.

A magnetic sensor system or any other sensor system may also comprise a temperature sensor to compensate for drifts of the primary physical quantity or sensor characteristic versus the secondary physical quantity temperature. With differential magnetic sensors it is even better to have a temperature sensor close to each magnetic sensor—in case the temperature is not homogeneous over the semiconductor die. These temperature sensors may also be used to detect manipulation or abnormal ambient or operation conditions (ninth criterion). Such a manipulation may be that someone heats up the sensor circuit with a hot air gun or with a cigarette lighter or blowtorch. Since the sensor system usually also has an oscillator on board, which defines a time-frame (e.g. for spinning current operation of Hall plates or to define a time discrete signal processing or to drive a digital circuit to process the data or to define time slots used in a data transmission protocol) one may also combine temperature and magnetic field information to detect abnormal ambient conditions. A manipulation is likely and an abnormal ambient condition is detected if the temperature leaves some specified band (too low or too high temperature). Furthermore, a manipulation is likely and an abnormal ambient condition is detected if the spatial temperature gradient over the die is too large. Finally a manipulation is likely and an abnormal ambient condition is detected if the rate of change of temperature or the temporal gradient of the temperature is too large: e.g. in an energy meter it is not common that the temperature rises by 100° C. within 1 second unless the current is too large—this may be used to detect a manipulation with some open flame.

Precise magnetic sensors often need some kind of on-board mechanical stress sensor as a secondary sensor, which measures the mechanical stress on the semiconductor die. This is used by the signal processing circuit 110 to compensate for drifts of the sensor characteristic caused by changes in mechanical stress. Manipulation at constant temperature or moderate temperature change may be done, e.g., by etching off parts of the package with e.g. sulfuric acid or by mechanically scratching, cutting, pressing, milling or grinding off parts of the sensor package. It may also be done by deliberately changing the moisture content of the mold compound of the sensor package by drying it or wetting it. All these manipulations result either in a sudden or in a significant change of mechanical stress on the die and this can be detected by the on-board stress sensors. The evaluation circuit 130 can be adapted to detect a manipulation or an abnormal ambient condition, if the mechanical stress on the die changes too much, or if a rate of stress changes, i.e. a change of stress divided by time, or a temporal gradient of the mechanical stress is too high.

In the following further aspects of the packaging of a magnetic field current sensor circuit or magnetic field current sensor package as shown in FIG. 5A will be described. However it should be noted that these explanations apply in a corresponding manner to other current sensor embodiments or other sensors in general.

Figure 5B:
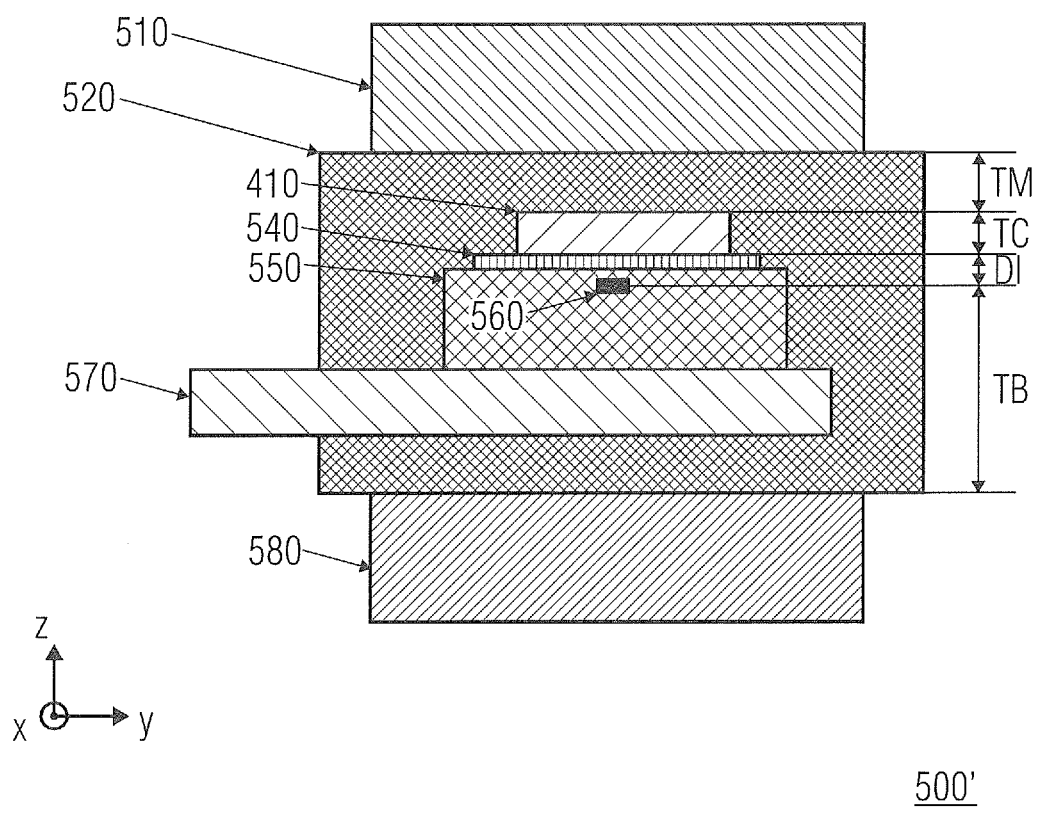
FIG. 5B shows a cross-sectional view of a magnetic field current sensor package with two external sources for disturbing the magnetic field.

FIG. 5B shows a package 500' for an integrated current sensor, or in other words, a current sensor package 500'. The current sensor package 500' comprises a semiconductor die 550 comprising a magnetic field sensor 560, for example, one of the magnetic field sensor elements 120, 220 or 620 as shown in FIG. 5A. The current sensor package 500' comprises furthermore a conductor or primary conductor 410 through which the current I to be measured flows. A dielectric isolation layer 540 is placed between the conductor 410 and the semiconductor die 550 to provide a voltage isolation between the high current 410 and the sensor circuit or the magnetic field sensor 560. The semiconductor die 550 is mounted on a substrate 570 or on a lead frame 570. All the aforementioned parts are covered by a mold compound 520. The mold compound 520 has the purpose to protect the sensor circuit, and in particular the current conductor and the semiconductor die, from the environment, for example, from light, moisture or from mechanical influences. With regard to the current sensor package 500' as shown in FIG. 5, there are now two possibilities to position a source of disturbing or unwanted physical quantity near to the sensor element or sensor elements. On one hand, the source of disturbing physical quantities can be arranged on top of the package, as depicted with reference sign 510 or below the package, as depicted with regard to reference sign 580. Denoting the vertical distance (in z-direction) between the sensor element 560 and a bottom surface of the current conductor 410 by DI, the vertical thickness of the current conductor itself by TC, the vertical thickness of the mold compound above the conductor (with regard to the orientation of FIG. 5B) by TM and the vertical distance between the sensor element 560 and the bottom surface of the package by TB, the disturbing source 510, 580 has a vertical distance to the sensor element 560 of either TB or DI+TC+ TM. In any case, when designing the package, these distances can be chosen such that they are much larger than DI, and, therefore, the spatial in-homogeneity of the disturbing physical quantities impacting on the sensor 560 and generated by the external sources 510 or 580 is less pronounced than the spatial in-homogeneity of the wanted physical quantities generated by the conductor 530 and impacting on the sensor 560.

In certain embodiments according to FIG. 5B, the vertical distance DI can be about 10 micrometers to 100 micrometers in case the current conductor 540 has a vertical thickness of about TC=1 mm. In case the vertical thickness of a mold material on top of the current conductor is about TM=0.3 mm, the minimum distance between the disturbing source 510 and the sensor elements is DI+TC+TM=1.4 mm. In other words, the minimum distance is about 14 times larger than the distance DI between the current conductor and the sensor elements. Such encapsulations are shown in FIG. 5B, can, for example, be used with current sensors 500 as shown in FIG. 5A.

Therefore, embodiments of the current sensor package may comprise an encapsulation or mold body, wherein an outer surface of the encapsulation of mold body is arranged such that a minimum distance between the outer surface and any of the magnetic field sensor elements is more than 10 times, more than 20 times or more than 30 times larger than a maximum distance between the current conductor through which the current to be measured flows and any of the magnetic field sensor elements.

Figure 5C:
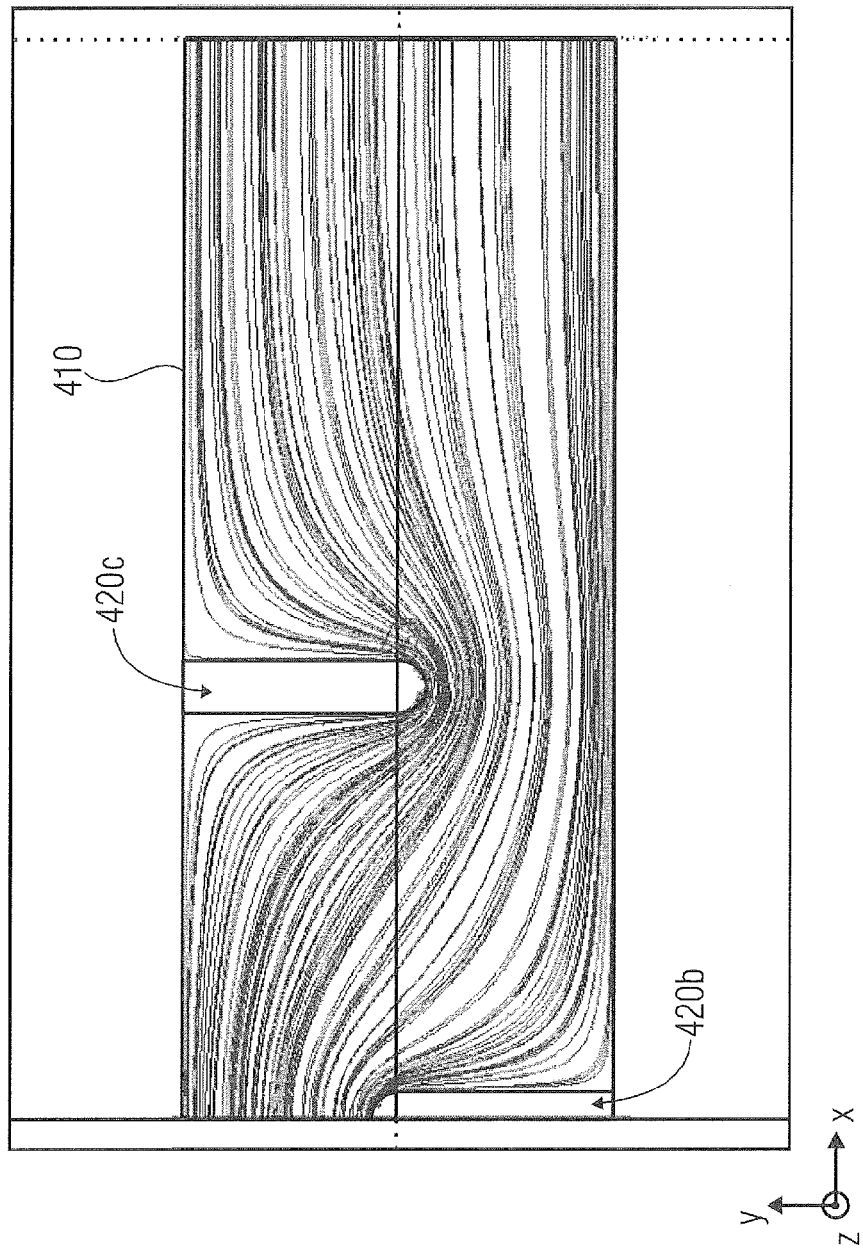
FIG. 5C shows an exemplary current density distribution in a part of the primary conductor of a magnetic field current sensor according to FIG. 5A.
Figure 5D:
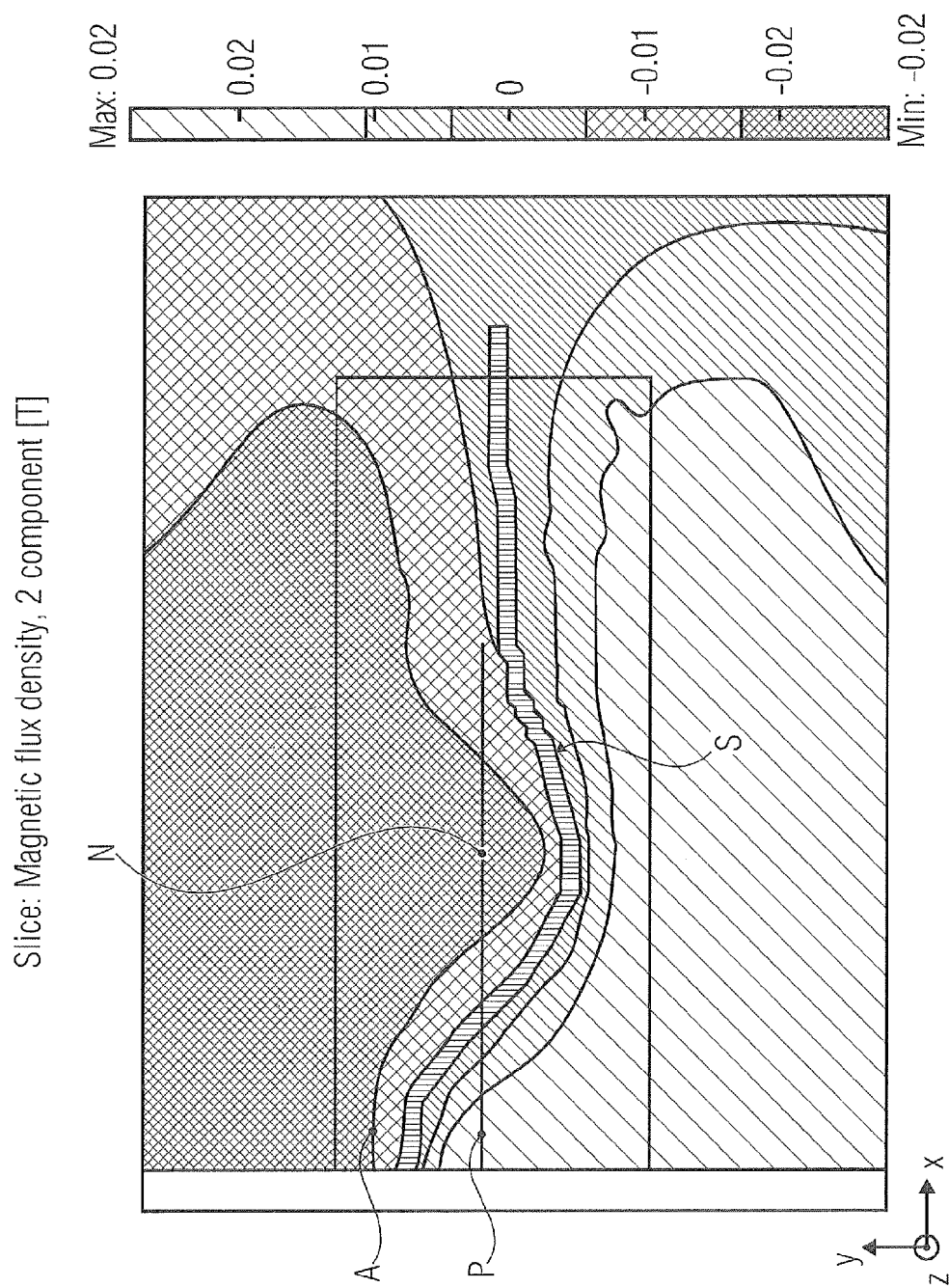
FIG. 5D shows an exemplary magnetic flux density distribution of the vertical component of the magnetic field for a part of the magnetic field current sensor according to FIG. 5A.

FIG. 5C shows a plane view of a right half or part of a conductor 410 as shown in FIG. 5A. The left half or part is mirror symmetric to the right half, as shown in FIG. 5A. FIG. 5C shows the current stream lines and how they bend around the slots. FIG. 5D shows the corresponding vertical component or z-component of the magnetic flux density 30 micrometers above or below the conductor 410. The point of the strongest positive magnetic field or Bz-field is indicated by reference sign P, the point of the strongest negative Bz-field is indicated by N, and the locations of vanishing Bz-field are indicated by a snake-like figure labeled S. At locations below (with reference to the figure) the snake-line S have positive magnetic field and locations above the snake-line S have negative magnetic field. Thus the field at point A has a large magnitude but a negative sign. The intensity of the Bz-field in z-direction is shown on the right hand side legend extending from −0.02 T(Tesla) to +0.02 T. As can be seen from FIGS. 5C and 5D, it is advantageous to place the magnetic field sensors H2 and H3 (see FIG. 5A) at the spots or locations P and N. The straight perpendicular lines between P and N and between P and A are those paths on which the highest inhomogeneities, i.e. the steepest slopes or largest spatial derivatives of the magnetic field generated by the current flowing through the conductor, occur. It is very difficult for manipulators to provide external disturbing sources that produce magnetic fields which have similar inhomogeneities along these paths. Therefore, embodiments of the apparatus or sensor circuit comprise one or more sensor elements placed along these paths to optimize a detection of external disturbances.

The evaluation circuit 130 can be adapted, for example, to compare all readings of these sensor elements with the aforementioned spatial pattern, which would be caused by a current thorough the conductor, and if significant differences from this theoretical pattern occur, the evaluation circuit 130 determines that there is a significant disturbance present and outputs the abnormal operation condition signal to the output port 190.

According to one embodiment of the sensor system or sensor circuit, one Hall plate is placed or arranged at spot P and another Hall plate at spot N. In this case, the current flowing through the conductor can be determined by the signal processing circuit 110 as a linear combination of the magnetic field values detected by the two sensor elements H2 and H3 arranged at spot P and spot N.

In addition, it is possible to find another linear combination which is independent of the current. This second linear combination is computed by the evaluation circuit 130 and compared with a reference value. If the discrepancy or difference is too large, the evaluation circuit signals the "abnormal operation condition" at the output port 190.

A further embodiment of the sensor system comprises a Hall plate at spot P and another Hall plate at line S. The evaluation circuit 130 can then be adapted to compare both values, a value of the sensor signal measured at spot P and the value of the sensor signal measured at line S, and if the difference is too small and at the same time the value at spot P indicates a medium or large current, the evaluation circuit signals "abnormal operating condition" at the output port 190.

Even more robust sensor systems which are more robust or reliable with regard to detecting external disturbances comprise sensor elements which are not only located along a straight line 590, as shown in FIG. 5A. Instead, these embodiments have sensor elements which span the entire x-,y-plane. The advantage of such arrangements is that it is much easier to manipulate the system, if the external field only needs to produce well-defined disturbances along a single direction, for example a one-dimensional disturbance along the x-axis, yet it is more difficult to produce well-defined disturbances with accurate inhomogeneities along two directions, particularly along two perpendicular directions, for example, along the x-axis and along the y-axis. Therefore, further embodiments of the above example of a current sensor comprise three Hall plates, wherein the first Hall plate is arranged at spot P, the second Hall plate is shifted only in x-direction (e.g. the second whole plate is arranged at location or spot N), and the third Hall plate is shifted only in y-direction (e.g. the third whole plate is arranged at spot A). Based on these three different spots or three different measurements, a first linear combination of these three sensor readings can be determined, which is proportional to the current to be measured (e.g. the total signal function as shown in FIG. 5A), while a second linear combination is independent on the current to be measured, e.g. is determined such that the wanted magnetic field parts of the current to be measured cancel each other out and only unwanted or disturbing magnetic field parts remain, and which are evaluated to detect whether an abnormal operation condition is present. The second linear combination can, for example, be compared by the evaluation circuit with the first linear combination and with other reference values to decide whether an abnormal operating condition is present. It should be noted that with three sensor elements or three sensor readings, there are two linear combinations available, which are independent of the current and which are indicative of abnormal operating conditions.

In another embodiment, the sensor elements may be placed also mirror symmetric above the left part of the conductor, which is not shown in FIGS. 5C and 5D. As mentioned before, a further or other Hall plate can be arranged at spot N' which corresponds to the position of the Hall plate H1 of FIG. 5A.

Summarizing the aforementioned, there are a lot of possibilities to place the sensor elements to detect abnormal operating conditions. The optimum placement of the sensor elements is the one that gives the largest differences in reading or sensing values divided by spacing, as described based on FIG. 5D with regard to the combination of spots P and N on one hand and P and A on the other hand. This is identical to the fact that the sensor elements should be placed such that they sense the largest spatial derivatives of the ambient or disturbing physical quantity. If at least three sensor elements are used, they are, for example, placed along at least two, preferably orthogonal directions.

Therefore, further embodiments of the current sensor circuit may comprise a third magnetic field sensor element as third primary sensor element adapted to produce a third sensor signal, wherein the first, second and third magnetic field sensor elements are not arranged on a straight line, or are arranged such that the first and the second primary sensor element define a first dimension, and the first and third primary sensor element define a second dimension that is orthogonal to the first dimension, and wherein the signal processing circuit is adapted to process the first, second and third sensor signal to obtain the measurement signal according to a differential measurement principle.

If at least four sensor elements are used, they are placed along three, preferably orthogonal directions, which is difficult for ordinary CMOS technologies, however, it is sometimes possible to arrange sensor elements on several surfaces of a semiconductor die, for example, on a top side and a rear side of the die or also along the circumference.

Therefore, further embodiments of the current sensor circuit may comprise a fourth magnetic field sensor element as fourth primary sensor element adapted to produce a fourth sensor signal, wherein the first, second and third magnetic field sensor elements are not arranged on the same two-dimensional plane, or are arranged such that the first and the second primary sensor element define a first dimension, the first and third primary sensor element define a second dimension that is orthogonal to the first dimension, and the first and the fourth primary sensor element define a third dimension that is orthogonal to the first and second dimension, and wherein the signal processing circuit is adapted to process the first, second, third and fourth sensor signal to obtain the measurement signal according to a differential measurement principle.

The larger the differences of the primary physical quantity to measure (e.g. the magnetic field of the current through the conductor in case of a current sensor) or, in other words, the more inhomogeneous the spatial distribution of the physical quantity to be measured between the locations of the sensor elements is, the more reliable the detection of abnormal operating conditions or disturbing sources is.

This requires certain prerequisites on the source, which generates the primary physical quantity.

Therefore, embodiments of the apparatus or sensor circuit comprising a current sensor comprise a conductor which generates spatially inhomogeneous magnetic fields. For example, a current sensor produces inhomogeneous fields, if its conductor is a thin wire: then the fields decay with 1/r, r being the radial distance to the center of the wire, and for radial r like, for example, 100 micrometers a strong in-homogeneity can be obtained. For larger currents, the conductor needs to be a planar conductor, or sheet-like, in order to have sufficiently low electrical resistance. In this case, fine slots or notches in the plane conductor cause inhomogeneities of the current and consequently also inhomogeneities of the magnetic field, as described based on FIGS. 5A to 5D.

In case of a speed sensor, the apparatus or sensor circuit comprises a target wheel with fine teeth or small magnetic domains.

It should be further noted that embodiments of the evaluation circuit evaluate the sensor signal 120$b$, i.e., do not only pass the sensor signal to the output port 190. In other words, in case the sensor element 120 is a magnetic field sensor, the evaluation circuit does not provide an output signal 130$b$ representing the measured magnetic field, or in case the sensor element 120 is a temperature sensor, the evaluation circuit does not output a signal 130$b$ representing the measured temperature. Embodiments of the evaluation circuit evaluate the sensor signal 120$b$ and provide, for example, in a rudimentary case only a binary signal indicating whether a normal operating condition is present or not, e.g. a binary signal with a first value (e.g. TRUE) indicating a normal operation condition and with a second value (e.g. FALSE) indicating an abnormal operating condition. Further embodiments may not only distinguish between a normal operating condition and an abnormal operating condition but may indicate different degrees of "abnormal" conditions by distinguishing between three or more values, wherein e.g. only one of these values indicates a normal operating condition and the other values indicate different degrees of abnormal operating conditions. Such embodiments of the evaluation circuit are adapted to output discrete values or discrete abnormal operating condition values. The number of different discrete values is typically small, for example, smaller than a dozen. The number of discrete values of the signal 130$b$ can, for example, correspond with the redundancy of the sensor elements. For example, in case of three sensors, one primary sensor signal is produced and two other conditions remain which can be used to indicate different violations of normal operating conditions, wherein, in this case, four different signals or warnings can be given: a first kind of violation, a second kind of violation, both conditions for a normal operating condition (NOC) are not fulfilled, or normal operating conditions are fulfilled.

In the following a method or algorithm performed by an embodiment of the evaluation circuit to determine whether a normal operation conditions (NOC) is present ("NOC=true") or not ("NOC=false", i.e. abnormal operation condition is present) is described.

The signal 110$b$ is computed by the signal processing circuit in the most reliable way, typically it uses all or most sensor elements for this calculation. The evaluation circuit checks if signal 110$b$ is within the required boundaries or a predetermined range of measurement values. For example, if the system is a current sensor and the current is too high then 110$b$ is too high. Then this is already enough to output via signal 130$b$ "NOC=false".

In case the measurement signal is within the predetermined range, the evaluation circuit evaluates one or all sensor signals 120$b$, 110$a$, etc, for example in an iterative manner.

The evaluation circuit starts with evaluating the sensor signal of the first sensor of a plurality of sensors arranged at different locations, by checking if the signal of the first sensor element is within a narrow range centred at a value which is caused by the physical quantity corresponding to the value of signal 110$b$. E.g., in case of a current sensor the system knows the value of the signal of the first sensor element if a current of a certain amount indicated by the signal 110$b$ flows through the conductor. If the signal of the first sensor element is outside this predetermined range, the output 130$b$ of the evaluation circuit is set to "NOC=false" to indicate an abnormal operation condition. The predetermined narrow range can be a fixed value or more often a percentage of a fixed value where the percentage depends on the signal 110$b$. Yet, often one has to account for the size of the measurand (at low currents the percentual range has to be less narrow because of inaccuracies of the system like noise and unavoidable small background fields).

Afterwards, the evaluation circuit repeats the aforementioned steps for the sensor signal of the second sensor element, afterwards the third one, and so on. Thus, the evaluation circuit evaluates each of the sensor signals of the plurality of sensor elements. As soon as one sensor signal does not fulfil the normal operation criterion, i.e. is not consistent, the evaluation circuit may stop the iteration and output the abnormal operation condition signal or may continue to check if further sensor signals are also not consistent.

In the following an example for a current sensor according to FIGS. 5A to 5D will be explained on exemplary values. It is assumed that the slots of the conductor are shaped in such a way and the thicknesses and vertical distances are such that a current of 1 A gives 100 µT at sensor P, −80 µT at sensor N and N' (where N' is placed at the mirror symmetric location above the left half of the conductor not shown in FIG. 5D), and −90 µT at sensor A. If one denotes the magnetic field at P with BP, at N with BN, at N' with BN', and at A with BA the signal 110b is computed by I=(3*BP−BN−BN'−BA)/(550 µT/A), where I denotes the estimated value of the current, i.e. the measurement result 110b. It is further assumed that the sensor has a maximum peak current of 100 A: higher currents cannot be measured because the amplifiers in the circuit or the sensor elements would saturate. The evaluation circuit EC first compares, if I is between −100 A and +100 A: if not, then there is an abnormal operating condition and "NOC=false" is output via signal 130b and port 190; if yes, a normal operation condition is present and "NOC=true" can be output via signal 130b and port 190. Next the evaluation circuit compares BP with I*100 µT/A, because at location P the field should be 100 µT per amp. If the difference is too large: "NOC=false" is output via signal 130b and port 190. Next the evaluation circuit EC compares BN with I*(−80)µT/A, because at location N the field should be −80 µT per amp. If the difference is too large: "NOC=false" is output via signal 130b and port 190. Next the evaluation circuit EC compares BN' with I*(−80)µT/A, because at location N' the field should be −80 µT per amp. If the difference is too large: "NOC=false" is output via signal 130b and port 190. Next the evaluation circuit EC compares BA with I*(−90)µT/A, because at location A the field should be −90 µT per amp. If the difference is too large: "NOC=false" is output via signal 130b and port 190. At this point the evaluation circuit EC has compared all individual sensor signals, whether they are consistent with the estimated value I or measurement signal. In case of consistency the evaluation circuit outputs "NOC=true" via port 190, in the opposite case the evaluation circuit outputs "NOC=false" via signal 130b and the port 190.

It is possible to skip checking one of these sensors individually, because its information is already contained in the estimation of I, which is checked at the start by the evaluation circuit.

Therefore, embodiments of the invention provide a sensor circuit, 100, 200, 300, 400, 500, comprising: a signal processing unit 110 adapted to process at least one sensor signal 120b of a plurality of sensor signals generated by at least one sensor element 120 to obtain a measurement signal 120b; and an evaluation circuit 130 adapted to evaluate the at least one sensor signal 120b of the plurality of sensor signals to derive a signal indicating an abnormal operating condition in case the at least one sensor signal does not fulfill a predetermined normal operation criterion and wherein the predetermined normal operation criteria defines a predetermined relation between a value of the at least one sensor signal and a value of at least one other sensor signal of the plurality of sensor signals (that is due to a predetermined temporal or spatial relation of the at least one sensor signal and the at least one other sensor signal) during a normal operation, or the relation between a value of the at least one sensor signal and a value of a measurement signal during a normal operation (that is also due to a predetermined temporal or spatial relation of the at least one sensor signal and the at least one other sensor signal a both have been used to determine the measurement signal).

It should be further noted that embodiments of the evaluation circuit can be adapted to perform the evaluation during a test mode and during a normal operation mode. The apparatus or sensor circuit can for example, be switched into a test mode to test, e.g. the functionality of the individual sensor elements, the signal processing unit and/or the evaluation circuit. During this test mode the circuit can also be calibrated by applying a defined current and sampling the readings of all individual sensor elements. Due to manufacturing tolerances it may happen that e.g. the readings of sensors N and its mirror symmetric counter part N' in FIG. 5D are not identical. The sampled values can be stored in a memory, which is part of the system, and later on during operation in the field the evaluation circuit may used these stored reference values to judge if "NOC=false" or "NOC=true". After testing the apparatus or sensor circuit can be switched to the operational mode, where the apparatus or sensor circuit performs its normal or primary operation, i.e. the processing of the input and sensor signals to obtain the output signal or measurement signal, while at the same time the evaluation circuit monitors the normal operation conditions and signals an abnormal operating condition in case the evaluation of the sensor signal reveals that it does not meet the normal operation conditions. The signal processing circuit and the evaluation circuit can be implemented as separate circuits or as one circuit that performs both tasks.

Once the manipulation is detected by the evaluation circuit 130, the evaluation circuit is adapted to communicate that an abnormal ambient or operation condition has been detected.

There are several strategies available for the evaluation circuit. The event can be stored in an on-board memory, e.g. EEPROM (Electronically Erasable Programmable Read Only Memory), and communicated later on, or it is communicated immediately through a dedicated pin, of the sensor or encoded into the output signal, e.g. by pulse code modulation (PCM) or pulse width modulation (PWM) or digital protocols like SPI, or as simple analog output voltage. In the case of an encoded output signal there should be information on the manipulation state also in the absence of manipulation or abnormal operation conditions, so that in case this information is missing the controller interprets it as "manipulation detected". Thus a fail-safe communication is provided.

In special cases it may be advantageous to feed the detected manipulation back into the system in order to immediately react on it: e.g. in credit cards it may be wished to immediately disable or lock the credit card if any manipulation is detected. In billing systems for energy meters it may by wished to output maximum current if manipulation is detected.

Parts of the invention may be used for other kind of sensors like pressure sensors, too. They may even be used for other kinds of integrated electronic circuits, which serve other purposes than sensing physical quantities: e.g. credit cards or communication circuits.

Depending on certain implementation requirements of the inventive methods, the inventive methods can be implemented in hardware or in software. The implementation can be performed using digital storage medium, in particular, a disc, CD, DVD or Blu-Ray disc having an electronically readable control signal stored thereon, which cooperates with a programmable computer system, such that an embodiment of the inventive methods is performed. Generally, an embodiment of the present invention is, therefore, a computer program product with a program code stored on a machine-readable carrier, the program code being operative for performing the inventive methods when the computer program product runs on a computer. In other words, embodiments of the inventive methods are therefore, a computer program having a program code for performing at least one of the inventive methods when a computer program runs on a computer.

The aforegoing was particularly shown and described with reference to the particular embodiments thereof, it will be understood by those skilled in the art that various other changes in the form and details may be made without departing from the spirit and scope thereof. It is therefore to be understood that various changes may be made in adapting to different embodiments without departing from the broader concept disclosed herein and comprehended by the claims that follow.

The invention claimed is:

1. An apparatus for determining a predetermined physical quantity from a source of the predetermined physical quantity, the apparatus comprising:
   a first sensor element and a second sensor element arranged at a first position and at a second position, respectively, with regard to the source, and being adapted to sense from the source the predetermined physical quantity, and to generate a first sensor signal and a second sensor signal, respectively, in response to the predetermined physical quantity;
   a signal processing circuit adapted to process the first sensor signal and the second sensor signal according to a first algorithm to obtain an output signal; and
   an evaluation circuit adapted to evaluate the first sensor signal and the second sensor signal according to a second algorithm to determine whether a predetermined normal operation criterion is fulfilled, and to obtain an indication signal indicating an abnormal operating condition in case the predetermined normal operation criterion is not satisfied.

2. The apparatus according to claim 1, comprising an output port adapted to output the indication signal via the output port.

3. The apparatus according to claim 2, wherein the output port is adapted to further output the output signal, or wherein a further output port is provided which is adapted to output the output signal.

4. The apparatus according to claim 1, comprising a package,
   wherein the sensor elements, the signal processing circuit and the evaluation circuit are encapsulated in the package by an encapsulating material.

5. The apparatus according to claim 1, wherein the first algorithm is a differential measurement algorithm comprising subtracting the first sensor signal or a multiple thereof from the second sensor signal or a multiple thereof, or vice versa.

6. The apparatus according to claim 5, wherein the second algorithm comprises adding the first sensor signal or a multiple thereof and the second sensor signal or a multiple thereof to obtain a sum value, and
   wherein the predetermined normal operation criterion defines a static maximum value, and wherein the evaluation circuit is adapted to generate the indication signal in case the sum value or a value derived therefrom is larger than the static maximum value, or
   wherein the predetermined normal operation criterion defines a static maximum magnitude, and wherein the evaluation circuit is adapted to generate the indication signal in case a magnitude of the sum value or of a value derived therefrom is larger than the static maximum magnitude, or
   wherein the predetermined normal operation criterion defines a dynamic maximum value based on at least the first sensor signal or the output signal, and wherein the evaluation circuit is adapted to generate the indication signal in case the sum value or a value derived therefrom is larger than the dynamic maximum value, or
   wherein the predetermined normal operation criterion defines a dynamic maximum magnitude based on at least the first sensor signal or the output signal, and wherein the evaluation circuit is adapted to generate the indication signal in case a magnitude of the sum value or a value derived therefrom is larger than the dynamic maximum magnitude.

7. The apparatus according to claim 1, wherein the second algorithm comprises determining a ratio of the first sensor signal over the second primary signal, or vice versa,
   wherein the predetermined normal operation criterion defines a maximum ratio, and wherein the evaluation circuit is adapted to generate the indication signal in case the ratio, a magnitude of the ratio or another value derived from the ratio is larger than the maximum ratio.

8. The apparatus according to claim 1, comprising a primary conductor producing the magnetic field by a current to be measured flowing through the primary conductor is different on both sensor elements,
   wherein the first and second sensor elements comprise a magnetic field sensor element and a second magnetic field sensor element arranged opposite to each other with the primary conductor arranged therebeween.

9. The apparatus according to claim 1, wherein at least the first sensor element and the second sensor element are integrated into a common semiconductor die.

10. A current sensor circuit comprising:
   an apparatus for determining a predetermined physical quantity from a source of the predetermined physical quantity, the apparatus comprising:
      a first sensor element and a second sensor element arranged at a first position and at a second position, respectively, with regard to the source, and being adapted to sense from the source the predetermined physical quantity, and
   to generate a first sensor signal and a second sensor signal in response to the predetermined physical quantity;
      a signal processing circuit adapted to process the first sensor signal and the second sensor signal according to a first algorithm to obtain an output signal; and
      an evaluation circuit adapted to evaluate the first sensor signal and the second sensor signal according to a second algorithm to determine whether a predetermined normal operation criterion is fulfilled, and to obtain an indication signal indicating an abnormal operating condition in case the predetermined normal operation criterion is not satisfied;
   wherein the predetermined normal operation criterion is derived from a predetermined temporal or spatial relation between a value of the first sensor signal from the first sensor element and a value of the second sensor signal from the second sensor element during a normal operation condition.

11. The current sensor circuit according to claim 10, wherein the apparatus further comprises a third sensor element adapted to produce a third sensor signal, wherein the first, second and third sensor elements are not arranged on a straight line, and wherein the signal processing circuit is adapted to process the first, second and third sensor signals to obtain the measurement signal according to a differential measurement principle.

12. A method for sensing a predetermined physical quantity from a source of the predetermined physical quantity, the method comprising:
- sensing the predetermined physical quantity from the source by a first sensor element and a second sensor element arranged at a first position and at a second position, respectively, with regard to the source, for producing a first sensor signal and a second sensor signal;
- processing the first sensor signal and the second sensor signal according to a first algorithm to obtain an output signal using a controller;
- processing the first sensor signal and the second sensor signal according to a second algorithm to determine whether a predetermined normal operation criterion is fulfilled; and
- obtaining an indication signal indicating an abnormal operating condition in case the predetermined normal operation criterion is not satisfied.

* * * * *